United States Patent
Walsh et al.

(10) Patent No.: US 9,526,850 B2
(45) Date of Patent: Dec. 27, 2016

(54) DOSE COUNTERS FOR INHALERS, INHALERS AND METHODS OF ASSEMBLY THEREOF

(71) Applicants: IVAX PHARMACEUTICALS IRELAND, Waterford (IE); NORTON (WATERFORD) LIMITED, Waterford (IE); TEVA PHARMACEUTICALS IRELAND, Waterford (IE)

(72) Inventors: Declan Walsh, County Kilkenny (IE); Derek Fenlon, County Wexford (IE); Simon Kaar, County Cork (IE); Jan Geert Hazenberg, County Kilkenny (IE); Daniel Buck, County Waterford (IE); Paul Clancy, Waterford (IE); Robert Charles Uschold, Leominster, MA (US); Jeffrey A. Karg, Hopkinton, MA (US)

(73) Assignees: IVAX Pharmaceuticals Ireland, Waterford (IE); Norton (Waterford) Limited, Waterford (IE); TEVA Pharmaceuticals Ireland, Waterford (IE)

( * ) Notice: Subject to any disclaimer, the term of this patent is extended or adjusted under 35 U.S.C. 154(b) by 0 days.

(21) Appl. No.: 14/103,353

(22) Filed: Dec. 11, 2013

(65) Prior Publication Data

US 2014/0096711 A1    Apr. 10, 2014

Related U.S. Application Data

(62) Division of application No. 13/110,532, filed on May 18, 2011, now Pat. No. 8,978,966.

(Continued)

(51) Int. Cl.
*G06M 1/06* (2006.01)
*A61M 11/00* (2006.01)
(Continued)

(52) U.S. Cl.
CPC .......... *A61M 15/0071* (2014.02); *A61M 11/00* (2013.01); *A61M 15/009* (2013.01);
(Continued)

(58) Field of Classification Search
USPC ............................. 235/8; 128/200.22, 200.23
See application file for complete search history.

(56) References Cited

U.S. PATENT DOCUMENTS 4,174,890 A * 11/1979 Johnson et al. ............ 353/26 A
4,669,838 A *  6/1987 Hibbard ..................... 353/26 A
(Continued)

FOREIGN PATENT DOCUMENTS

CA      2501726     9/2006
EP      1330280    11/2004
(Continued)

OTHER PUBLICATIONS

First Examination Report of counterpart New Zealand Patent Application No. 603466, dated Jul. 1, 2013.
(Continued)

*Primary Examiner* — Daniel Hess
(74) *Attorney, Agent, or Firm* — RatnerPrestia

(57) ABSTRACT

A manually operated metered dose inhaler includes a dose counter chamber including a dose display tape driven by a ratchet wheel which is driven in turn by an actuator pawl actuated by movement of a canister, the tape unwinding from a stock bobbin during use of the inhaler, a rotation regulator being provided for the stock bobbin and including a wavelike engagement surface with concavities which engage against control elements in the form of protrusions (Continued)

on resilient forks of a split pin thereby permitting incremental unwinding of the stock bobbin yet resisting excessive rotation if the inhaler is dropped onto a hard surface.

10 Claims, 17 Drawing Sheets

Related U.S. Application Data

(60) Provisional application No. 61/345,763, filed on May 18, 2010, provisional application No. 61/417,659, filed on Nov. 29, 2010.

(51) Int. Cl.
*A61M 15/00* (2006.01)
*G06M 1/24* (2006.01)

(52) U.S. Cl.
CPC .... *A61M 15/0025* (2014.02); *A61M 15/0026* (2014.02); *A61M 15/0065* (2013.01); *A61M 15/0078* (2014.02); *G06M 1/246* (2013.01); *A61M 2202/064* (2013.01); *A61M 2205/6063* (2013.01); *A61M 2207/00* (2013.01); *A61M 2207/10* (2013.01); *Y10T 29/49* (2015.01); *Y10T 29/49764* (2015.01); *Y10T 29/49826* (2015.01)

(56) References Cited

U.S. PATENT DOCUMENTS

| | | | |
|---|---|---|---|
| 4,687,359 A * | 8/1987 | Barrus et al. ............... 400/218 |
| 5,482,030 A | 1/1996 | Klein |
| 5,861,911 A | 1/1999 | Oosaka |
| 6,446,627 B1 | 9/2002 | Bowman et al. |
| 6,718,972 B2 | 4/2004 | O'Leary |
| 8,418,690 B2 | 4/2013 | Power |
| 8,474,448 B2 | 7/2013 | Oi |
| 2002/0047021 A1 | 4/2002 | Blacker et al. |
| 2002/0078949 A1 | 6/2002 | OLeary |
| 2002/0078950 A1 | 6/2002 | OLeary |
| 2003/0209239 A1 | 11/2003 | Rand |
| 2004/0095746 A1 | 5/2004 | Murphy |
| 2005/0028815 A1 | 2/2005 | Deaton et al. |
| 2005/0087191 A1 | 4/2005 | Morton et al. |
| 2006/0096594 A1 | 5/2006 | Bonney et al. |
| 2006/0107979 A1 | 5/2006 | Kim |
| 2007/0062518 A1 | 3/2007 | Geser |
| 2008/0242465 A1 | 10/2008 | Strobel |
| 2009/0178678 A1 | 7/2009 | O'Leary |
| 2010/0089395 A1 | 4/2010 | Power |
| 2010/0218759 A1 | 9/2010 | Anderson et al. |
| 2011/0041845 A1* | 2/2011 | Solomon ............. A61M 15/009 128/203.12 |
| 2012/0006322 A1 | 1/2012 | Anderson |

FOREIGN PATENT DOCUMENTS

| | | |
|---|---|---|
| EP | 1486227 | 12/2004 |
| GB | 2320489 A | 6/1998 |
| JP | 02502129 | 7/1990 |
| JP | 450059 | 8/1992 |
| JP | 07100205 | 4/1995 |
| JP | 10504220 | 4/1998 |
| JP | 2002528144 | 9/2002 |
| JP | 2004501685 | 1/2004 |
| JP | 2008094103 | 4/2008 |
| JP | 2008261423 | 10/2008 |
| JP | 2009233308 | 10/2009 |
| JP | 2009257392 | 11/2009 |
| JP | 2010096308 | 4/2010 |
| WO | 8909078 | 10/1989 |
| WO | 9628205 | 9/1996 |
| WO | WO 9828033 | 7/1998 |
| WO | 9936115 | 7/1999 |
| WO | 03101514 | 12/2003 |
| WO | 2005102430 | 11/2005 |
| WO | WO 2006/062449 | 6/2006 |
| WO | 2007012861 | 2/2007 |
| WO | 2007062518 | 6/2007 |
| WO | WO 2008/023019 | 2/2008 |
| WO | WO 2008119552 | 10/2008 |
| WO | 2011012325 | 2/2011 |
| WO | 2011012327 | 2/2011 |

OTHER PUBLICATIONS

Entire patent prosecution history of U.S. Appl. No. 14/699,567, filed Apr. 29, 2015, entitled, "Dose Counter for Inhaler and Method for Counting Doses."
Entire patent prosecution history of U.S. Appl. No. 14/699,578, filed Apr. 29, 2015, entitled, "Dose Counter for Inhaler Having a Bore and Shaft Arrangement."
Entire patent prosecution history of U.S. Appl. No. 14/699,584, filed Apr. 29, 2015, entitled, "Dose Counter for Inhaler Having an Anti-Reverse Rotation Actuator."
Entire patent prosecution history of U.S. Appl. No. 14/713,612, filed May 15, 2015, entitled, "Dose Counters for Inhalers, Inhalers and Methods of Assembly Thereof."
Entire patent prosecution history of U.S. Appl. No. 14/713,620, filed May 15, 2015, entitled, "Dose Counters for Inhalers, Inhalers and Methods of Assembly Thereof."
Entire patent prosecution history of U.S. Appl. No. 14/713,633, filed May 15, 2015, entitled, "Dose Counters for Inhalers, Inhalers and Methods of Assembly Thereof."
Entire patent prosecution history of U.S. Appl. No. 14/713,643, filed May 15, 2015, entitled, "Dose Counters for Inhalers, Inhalers and Methods of Assembly Thereof."
Entire patent prosecution history of U.S. Appl. No. 13/110,532, filed May 18, 2011, entitled, "Dose Counters for Inhalers, Inhalers and Methods of Assembly Thereof."
Entire patent prosecution history of U.S. Appl. No. 14/103,324, filed Dec. 11, 2013, entitled, "Dose Counters for Inhalers, Inhalers and Methods of Assembly Thereof."
Entire patent prosecution history of U.S. Appl. No. 14/103,343, filed Dec. 11, 2013, entitled, "Dose Counters for Inhalers, Inhalers and Methods of Assembly Thereof."
Entire patent prosecution history of U.S. Appl. No. 14/103,363, filed Dec. 1, 2013, entitled, "Dose Counters for Inhalers, Inhalers and Methods of Assembly Thereof."
Entire patent prosecution history of U.S. Appl. No. 14/103,392, filed Dec. 11, 2013, entitled, "Dose Counters for Inhalers, Inhalers and Methods of Assembly Thereof."
European Patent Office Communication, dated Apr. 24, 2014 of counterpart European Patent Application No. 11 010 211.8.
European Patent Office Communication, dated Apr. 24, 2014 of counterpart European Patent Application No. 11 010 212.6.

* cited by examiner

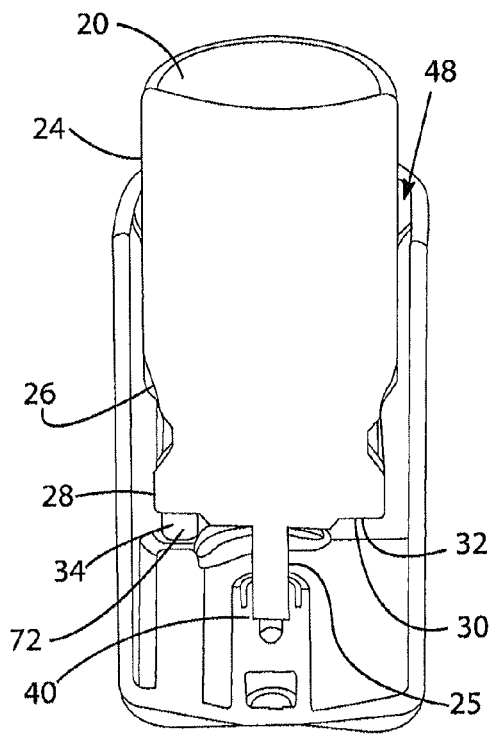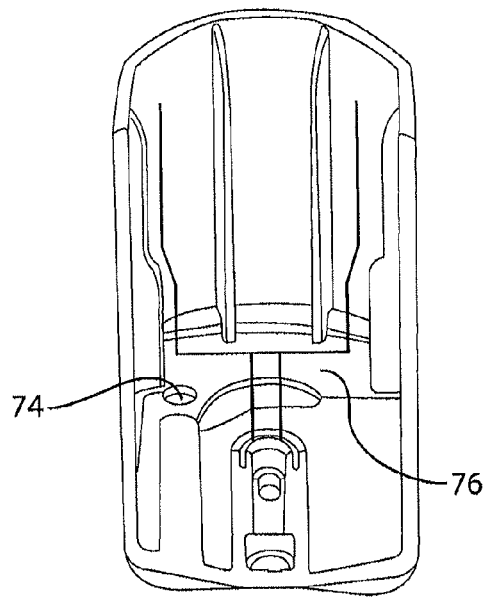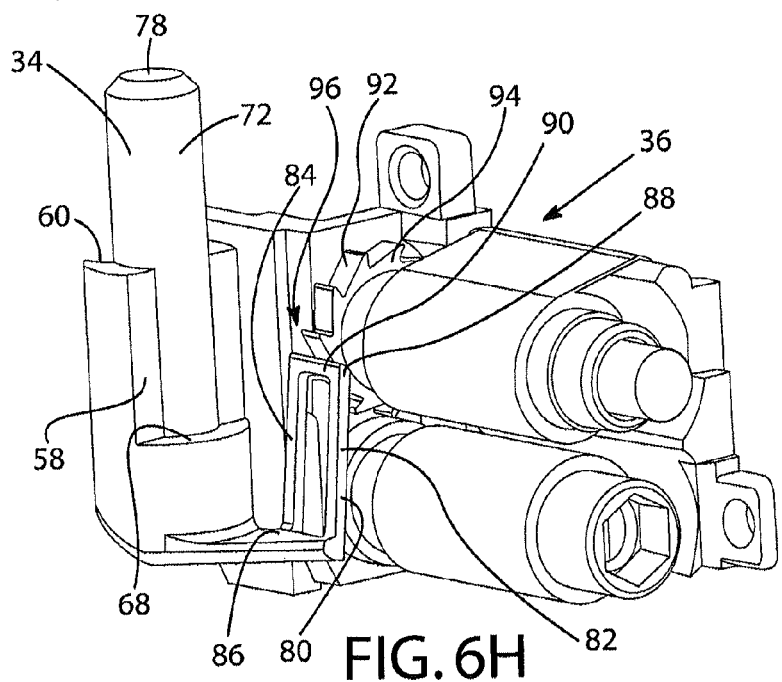

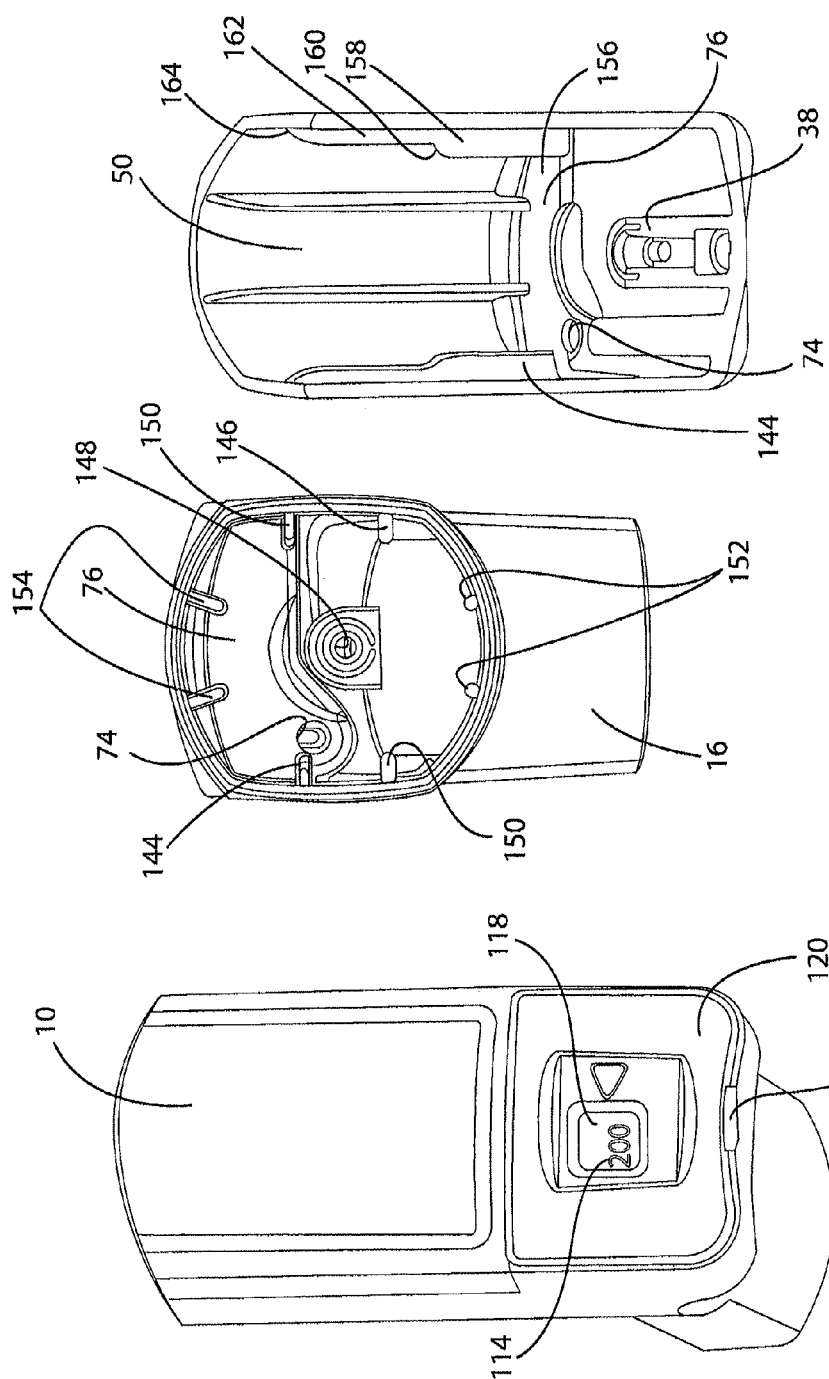

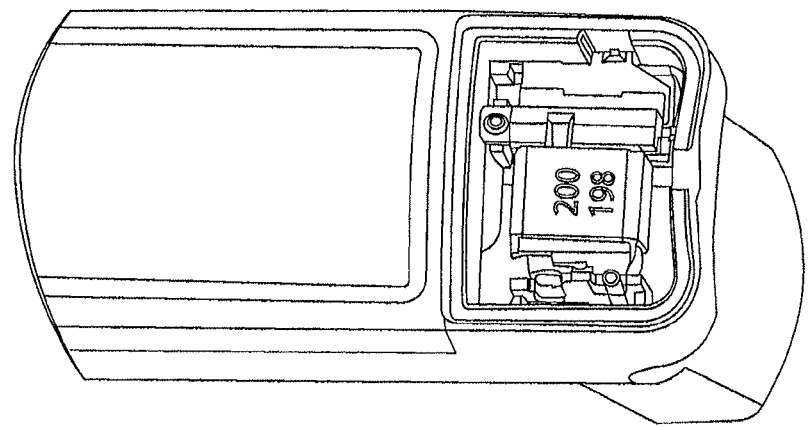
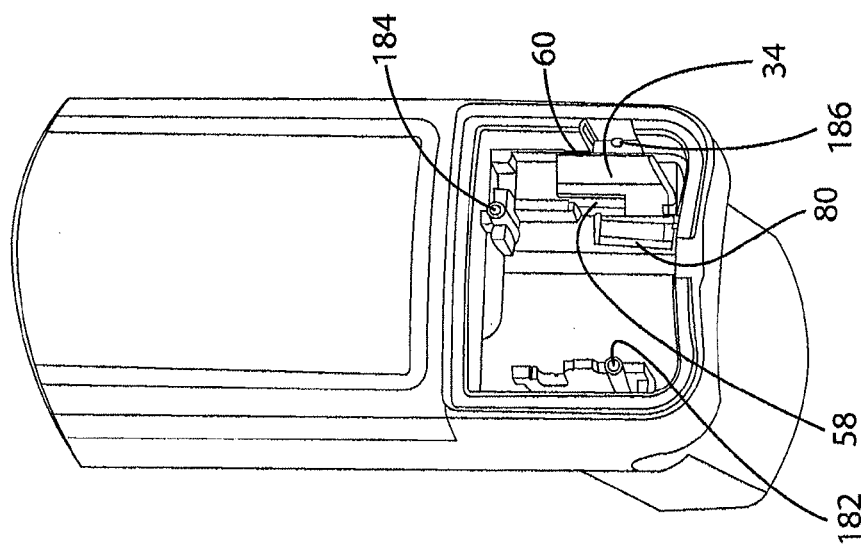
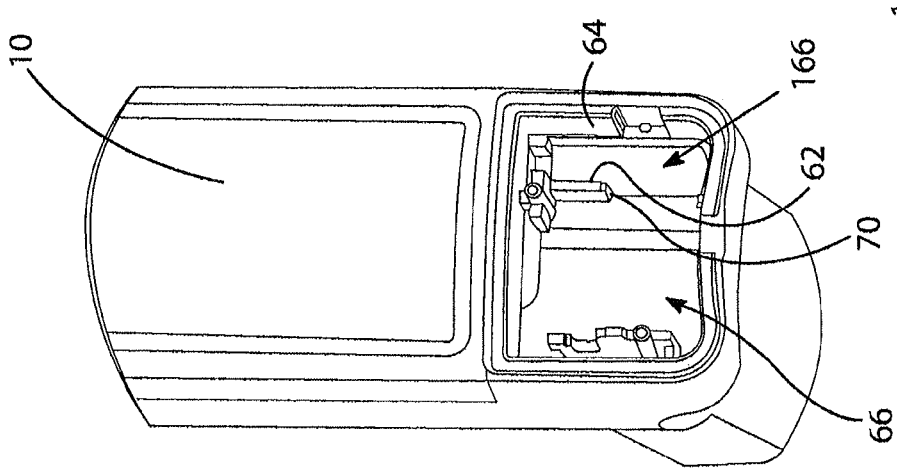
FIG. 8C
FIG. 8B
FIG. 8A

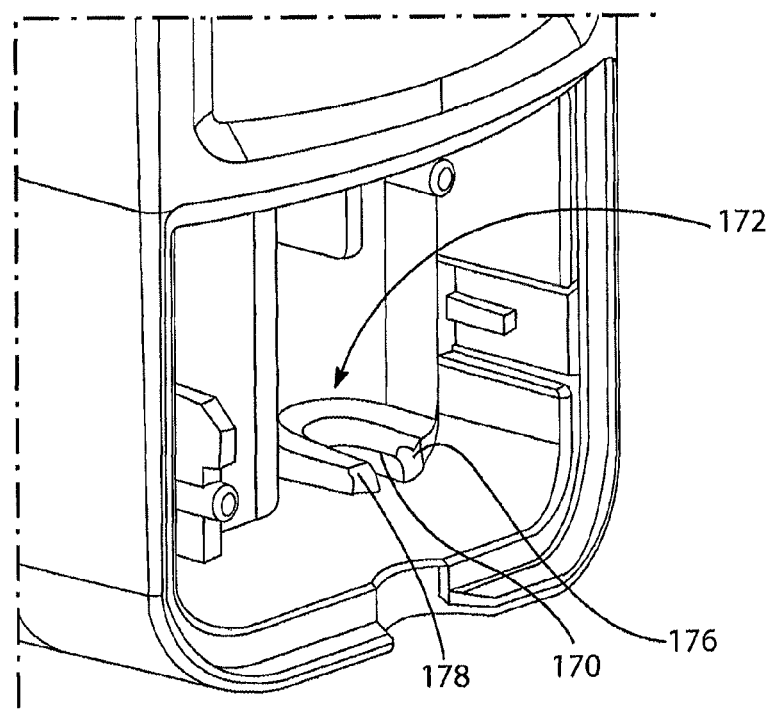
FIG. 12
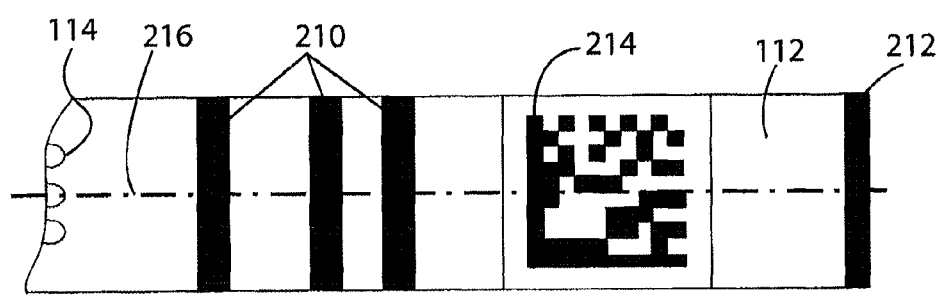
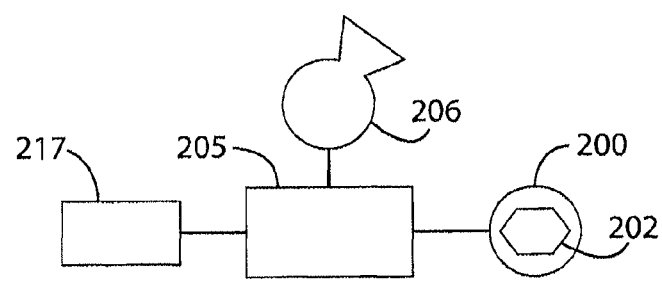
FIG. 13

DOSE COUNTERS FOR INHALERS, INHALERS AND METHODS OF ASSEMBLY THEREOF

CROSS-REFERENCE TO RELATED APPLICATIONS

This patent application is a divisional patent application of U.S. Non-Provisional patent application Ser. No. 13/110,532, filed May 18, 2011, which claims priority to U.S. Provisional Patent Application No. 61/345,763, filed May 18, 2010, and U.S. Provisional Patent Application No. 61/417,659, filed Nov. 29, 2010, each of which is incorporated herein by reference in its entirety for all purposes.

FIELD OF THE INVENTION

The present invention relates to dose counters for inhalers, inhalers and methods of assembly thereof. The invention is particularly applicable to metered dose inhalers including dry power medicament inhalers, breath actuated inhalers and manually operated metered dose medicament inhalers.

BACKGROUND OF THE INVENTION

Metered dose inhalers can comprise a medicament-containing pressurised canister containing a mixture of active drug and propellant. Such canisters are usually formed from a deep-dawn aluminium cup having a crimped lid which carries a metering valve assembly. The metering valve assembly is provided with a protruding valve stem which, in use is inserted as a push fit into a stem block in an actuator body of an inhaler having a drug delivery outlet. In order to actuate a manually operable inhaler, the user applies by hand a compressive force to a closed end of the canister and the internal components of the metering valve assembly are spring loaded so that a compressive force of approximately 15 to 30N is required to activate the device in some typical circumstances.

In response to this compressive force the canister moves axially with respect to the valve stem and the axial movement is sufficient to actuate the metering valve and cause a metered quantity of the drug and the propellant to be expelled through the valve stem. This is then released into a mouthpiece of the inhaler via a nozzle in the stem block, such that a user inhaling through the outlet of the inhaler will receive a dose of the drug.

A drawback of self-administration from an inhaler is that it is difficult to determine how much active drug and/or propellant are left in the inhaler, if any, especially of the active drug and this is potentially hazardous for the user since dosing becomes unreliable and backup devices not always available.

Inhalers incorporating dose counters have therefore become known.

WO 98/280733 discloses an inhaler having a ratchet mechanism for driving a tape drive dose counter. A shaft onto which tape is wound has a friction clutch or spring for restraining the shaft against reverse rotation.

EP-A-1486227 discloses an inhaler for dry powered medicament having a ratchet mechanism for a tape dose counter which is operated when a mouthpiece of the inhaler is closed. Due to the way in which the mouthpiece is opened and closed, and actuation pawl of the device which is mounted on a yoke, travels a known long stroke of consistent length as the mouthpiece is opened and closed.

WO 2008/119552 discloses a metered-dose inhaler which is suitable for breath-operated applications and operates with a known and constant canister stroke length of 3.04 mm+/−0.255 mm. A stock bobbin of the counter, from which a tape is unwound, rotates on a shaft having a split pin intended to hold the stock bobbin taut. However, some dose counters do not keep a particularly reliable count, such as if they are dropped onto a hard surface.

More recently, it has become desirable to improve dose counters further and, in particular, it is felt that it would be useful to provide extremely accurate dose counters for manually-operated canister-type metered dose inhalers. Unfortunately, in these inhalers, it has been found in the course of making the present invention that the stroke length of the canister is to a very large extent controlled on each dose operation by the user, and by hand. Therefore, the stroke length is highly variable and it is found to be extremely difficult to provide a highly reliable dose counter for these applications. The dose counter must not count a dose when the canister has not fired since this might wrongly indicate to the user that a dose has been applied and if done repeatedly the user would throw away the canister or whole device before it is really time to change the device due to the active drug and propellant reaching a set minimum. Additionally, the canister must not fire without the dose counter counting because the user may then apply another dose thinking that the canister has not fired, and if this is done repeatedly the active drug and/or propellant may run out while the user thinks the device is still suitable for use according to the counter. It has also been found to be fairly difficult to assembly some known inhaler devices and the dose counters therefor. Additionally, it is felt desirable to improve upon inhalers by making them easily usable after they have been washed with water.

The present invention aims to alleviate at least to a certain extent one or more of the problems of the prior art.

SUMMARY OF THE INVENTION

According to a first aspect of the present invention there is provided a dose counter for an inhaler, the dose counter having a counter display arranged to indicate dosage information, a drive system arranged to move the counter display incrementally in a first direction from a first station to a second station in response to actuation input, wherein a regulator is provided which is arranged to act upon the counter display at the first station to regulate motion of the counter display at the first station to incremental movements.

The regulator is advantageous in that it helps prevent unwanted motion of the counter display if the counter is dropped.

According to a further aspect of the present invention, the regulator provides a resistance force of greater than 0.1 N against movement of the counter display. According to still a further aspect of the present invention, the resistance force is greater than 0.3 N. According to yet a further aspect of the present invention, the resistance force is from 0.3 to 0.4 N.

Preferably, the counter comprises a tape.

Preferably, the tape has dose counter indicia displayed thereon. The first station may comprise a region of the dose counter where tape is held which is located before a display location, such as a display window, for the counter indicia.

The first station may comprise a first shaft, the tape being arranged on the first shaft and to unwind therefrom upon movement of the counter display.

The first shaft may be mounted for rotation relative to a substantially rotationally fixed element of the dose counter.

The regulator may comprise at least one projection which is arranged on one of the first shaft and the substantially rotationally fixed element and to engage incrementally with one or more formations on the other of the first shaft and the substantially rotationally fixed element.

At least two said projections may be provided. Exactly two said projections maybe provided.

Each projection may comprise a radiused surface.

The at least one projection may be located on the substantially fixed element which may comprise a fixed shaft which is fixed to a main body of the dose counter, the first shaft being rotationally mounted to the fixed shaft.

Preferably, the fixed shaft has at least two resiliently flexible legs (or forks). Each leg may have at least one said projection formed in an outwardly facing direction thereon, said one or more formations being formed on an inwardly facing engagement surface of the first shaft, said at least one projection being arranged to resiliently engage said one or more formations. Preferably, a series of said formations are provided. An even number of said formations may be provided. Eight to twelve of said formations may be provided. In one embodiment, ten said formations are provided.

Each said formation may comprise a concavity formed on an engagement surface. Each concavity may comprise a radiused surface wall portion which preferably merges on at least one side thereof into a flat wall portion surface. The engagement surface may include a series of said concavities, and convex wall portions of the engagement surface may be formed between each adjacent two said concavities, each said convex wall portion comprising a convex radiused wall portion.

Each convex radiused wall portion of each convex wall portion may be connected by said flat wall portion surfaces to each adjacent concavity.

The fixed shaft may comprise a split pin with fork legs and each projection may be located on a said fork leg.

The first shaft may comprise a substantially hollow bobbin.

Said at least one formation may be located on an inner surface of the bobbin. In other embodiments it may be located on an outer surface thereof. Said engagement surface may extend partially along said bobbin, a remainder of the respective inner or outer surface having a generally smooth journal portion along at least a portion thereof.

The drive system may comprise a tooth ratchet wheel arranged to act upon a second shaft which is located at the second station, the second shaft being rotatable to wind the tape onto the second shaft.

The second shaft may be located on a main body of the dose counter spaced from and parallel to the first shaft.

The ratchet wheel may be fixed to the second shaft is arranged to rotate therewith. The ratchet wheel may be secured to an end of the second shaft and aligned coaxially with the second shaft.

The dose counter may include anti-back drive system which is arranged to restrict motion of the second shaft. The anti-back drive system may include a substantially fixed tooth arranged to act upon teeth of the ratchet wheel.

According to a further aspect of the present invention, a dose counter includes an anti-back drive system which is arranged to restrict motion of the second shaft in a tape winding direction.

According to a further aspect of the present invention there is provided a shaft for holding counter tape in a dose counter for an inhaler, the shaft having an engagement surface including incrementally spaced formations located around a periphery thereof, the formations comprising a series of curved concavities and convex portions.

The shaft may comprise a hollow bobbin.

The engagement surface may be a generally cylindrical inwardly directed surface.

The engagement surface may include a flat surface wall portion joining each concavity and convex wall portion.

Each concavity may comprise a radiused wall portion.

Each convex wall portion may comprise a radiused wall portion.

Said concavities may be regularly spaced around a longitudinal axis of the shaft.

Said convex wall portions may be regularly spaced around a longitudinal axis of the shaft.

In some embodiments there may be from eight to twelve said concavities and/or concavities regularly spaced around a longitudinal axis thereof.

One embodiment includes ten said concavities and/or convex wall portions regularly spaced around a longitudinal axis of the shaft.

According to a further aspect of the present invention there is provided a shaft and counter tape assembly for use in a dose counter for an inhaler, the assembly comprising a rotatable shaft and a counter tape which is wound around the shaft and is adapted to unwind therefrom upon inhaler actuation, the shaft having an engagement surface which includes incrementally spaced formations located around a periphery thereof.

According to a further aspect of the present invention there is provided an inhaler for the inhalation of medication and the like, the inhaler including a dose counter as in the first aspect of the present invention.

A preferred construction consists of a manually operated metered dose inhaler including a dose counter chamber including a dose display tape driven by a ratchet wheel which is driven in turn by an actuator pawl actuated by movement of a canister, the tape unwinding from a stock bobbin during use of the inhaler, a rotation regulator being provided for the stock bobbin and comprising a wavelike engagement surface with concavities which engage against control elements in the form of protrusions on resilient forks of a split pin thereby permitting incremental unwinding of the stock bobbin yet resisting excessive rotation if the inhaler is dropped onto a hard surface.

According to another aspect of the present invention there is provided a dose counter for a metered dose inhaler having a body arranged to retain a medicament canister of predetermined configuration for movement of the canister relative thereto; the dose counter comprising: an incremental counting system for counting doses, the incremental counting system having a main body, an actuator arranged to be driven in response to canister motion and to drive an incremental output member in response to canister motion, the actuator and incremental output member being configured to have predetermined canister fire and count configurations in a canister fire sequence, the canister fire configuration being determined by a position of the actuator relative to a datum at which the canister fires medicament and the count configuration being determined by a position of the actuator relative to the datum at which the incremental count system makes an incremental count, wherein the actuator is arranged to reach a position thereof in the count configuration at or after a position thereof in the canister fire configuration.

This arrangement has been found to be highly advantageous since it provides an extremely accurate dose counter which is suitable for use with manually operated metered dose inhalers. It has been found that dose counters with these features have a failure rate of less than 50 failed counts per million full canister activation depressions. It has been found in the course of making the present invention that highly reliable counting can be achieved with the dose counter counting at or soon after the point at which the canister fires. It has been is covered by the present inventors that momentum and motion involved in firing the canister, and in some embodiments a slight reduction in canister back pressure on the user at the time of canister firing, can very reliably result in additional further motion past the count point.

The actuator and incremental counting system may be arranged such that the actuator is displaced less than 1 mm, typically 0.25 to 0.75 mm, more preferably about 0.4 to 0.6 mm, relative to the body between its location in the count and fire configurations, about 0.48 mm being preferred. The canister, which can move substantially in line with the actuator, can reliably move this additional distance so as to achieve very reliable counting.

The incremental count system may comprise a ratchet mechanism and the incremental output member may comprise a ratchet wheel having a plurality of circumferentially spaced teeth arranged to engage the actuator.

The actuator may comprise an actuator pawl arranged to engage on teeth of the ratchet wheel. The actuator pawl may be arranged to be connected to or integral with an actuator pin arranged to engage and be depressed by a medicament canister bottom flange. The actuator pawl may be generally U-shaped having two parallel arms arranged to pull on a central pawl member arranged substantially perpendicular thereto. This provides a very reliable actuator pawl which can reliably pull on the teeth of the ratchet wheel.

The incremental count system may include a tape counter having tape with incremental dose indicia located thereon, the tape being positioned on a tape stock bobbin and being arranged to unwind therefrom.

The actuator and incremental output member may be arranged to provide a start configuration at which the actuator is spaced from the ratchet output member, a reset configuration at which the actuator is brought into engagement with the incremental output member during a canister fire sequence, and an end configuration at which the actuator disengages from the ratchet output during a canister fire sequence.

The actuator may be arranged to be located about 1.5 to 2.0 mm, from its location in the fire configuration, when in the start configuration, about 1.80 mm being preferred.

The actuator may be arranged to be located about 1.0 to 1.2 mm, from its location in the fire configuration, when in the reset configuration, about 1.11 mm being preferred.

The actuator may be arranged to be located about 1.1 to 1.3 mm, from its location in the fire configuration, when in the end configuration, about 1.18 mm being preferred.

These arrangements provide extremely reliable dose counting, especially with manually operated canister type metered dose inhalers.

The main body may include a formation for forcing the actuator to disengage from the incremental output member when the actuator is moved past the end configuration. The formation may comprise a bumped up portion of an otherwise generally straight surface against which the actuator engages and along which it is arranged to slide during a canister firing sequence.

The dose counter may include a counter pawl, the counter pawl having a tooth arranged to engage the incremental output member, the tooth and incremental output member being arranged to permit one way only incremental relative motion therebetween. When the incremental output member comprises a ratchet wheel, the tooth can therefore serve as an anti-back drive tooth for the ratchet wheel, thereby permitting only one way motion or rotation thereof.

The counter pawl may be substantially fixedly mounted on the main body of the incremental count system and the counter pawl may be arranged to be capable of repeatedly engaging equi-spaced teeth of the incremental output member in anti-back drive interlock configurations as the counter is operated. The counter pawl may be positioned so that the incremental output member is halfway, or substantially halfway moved from one anti-back drive interlock configuration to the next when the actuator and incremental output member are in the end configuration thereof. This is highly advantageous in that it minimises the risk of double counting or non-counting by the dose counter.

According to a further aspect of the invention there is provided an inhaler comprising a main body arranged to retain a medicament canister of predetermined configuration and a dose counter mounted in the main body.

The inhaler main body may include a canister receiving portion and a separate counter chamber, the dose counter being located within the main body thereof, the incremental output member and actuator thereof inside the counter chamber, the main body of the inhaler having wall surfaces separating the canister-receiving portion and the counter chamber, the wall surfaces being provided with a communication aperture, an actuation member extending through the communication aperture to transmit canister motion to the actuator.

According to a further aspect of the present invention there is a provided an inhaler for metered dose inhalation, the inhaler comprising a main body having a canister housing arranged to retain a medicament canister for motion therein, and a dose counter, the dose counter having an actuation member having at least a portion thereof located in the canister housing for operation by movement of a medicament canister, wherein the canister housing has an inner wall, and a first inner wall canister support formation located directly adjacent the actuation member.

This is highly advantageous in that the first inner wall canister support formation can prevent a canister from rocking too much relative to the main body of the inhaler. Since the canister may operate the actuation member of the dose counter, this substantially improves dose counting and avoids counter errors.

The canister housing may have a longitudinal axis which passes through a central outlet port thereof, the central outlet port being arranged to mate with an outer canister fire stem of a medicament canister, the inner wall canister support formation, the actuation member and the outlet port lying in a common plane coincident with the longitudinal axis. Accordingly, this construction may prevent the canister from rocking towards the position of the dose counter actuation member, thereby minimising errors in counting.

The canister housing may have a further inner canister wall support formation located on the inner wall opposite, or substantially opposite, the actuation member. Accordingly, the canister may be supported against rocking motion away from the actuator member so as to minimise count errors.

The canister housing may be generally straight and tubular and may have an arrangement in which each said inner wall support formation comprises a rail extending longitudinally along the inner wall.

Each said rail may be stepped, in that it may have a first portion located towards a medicine outlet end or stem block of the canister housing which extends inwardly a first distance from a main surface of the inner wall and a second portion located toward an opposite end of the canister chamber which extends inwardly a second, smaller distance from the main surface of the inner wall. This may therefore enable easy insertion of a canister into the canister housing such that a canister can be lined up gradually in step wise function as it is inserted into the canister housing.

The inhaler may include additional canister support rails which are spaced around an inner periphery of the inner wall of the canister housing and which extend longitudinally therealong.

At least one of the additional rails may extend a constant distance inwardly from the main surface of the inner wall.

At least one of the additional rails may be formed with a similar configuration to the first inner wall canister support formation.

The dose counter may, apart from said at least a portion of the actuation member, be located in a counter chamber separate from the canister housing, the actuation member comprising a pin extending through an aperture in a wall which separates the counter chamber and the canister housing.

According to a further aspect of the present invention there is provided an inhaler for inhaling medicaments having: a body for retaining a medicament store; the body including a dose counter, the dose counter having a moveable actuator and a return spring for the actuator, the return spring having a generally cylindrical and annular end; the body having a support formation therein for supporting said end of the return spring, the support formation comprising a shelf onto which said end is engageable and a recess below the shelf.

This shelf and recess arrangement is highly advantageous since it allows a tool (such as manual or mechanical tweezers) to be used to place the return spring of the actuator onto the shelf with the tool then being withdrawn at least partially via the recess.

The shelf may be U-shaped.

The support formation may include a U-shaped upstanding wall extending around the U-shaped shelf, the shelf and upstanding wall thereby forming a step and riser of a stepped arrangement.

The recess below the shelf my also be U-shaped.

At least one chamfered surface may be provided at an entrance to the shelf. This may assist in inserting the actuator and return spring into position.

A further aspect of the invention provides a method of assembly of an inhaler which includes the step of locating said end of said spring on the shelf with an assembly tool and then withdrawing the assembly tool at least partly via the recess. This assembly method is highly advantageous compared to prior art methods in which spring insertion has been difficult and in which withdrawal of the tool has sometimes accidentally withdrawn the spring again.

The cylindrical and annular end of the spring may be movable in a direction transverse to its cylindrical extent into the shelf while being located thereon.

According to a further aspect of the present invention there is provided an inhaler for inhaling medicament, the inhaler having a body for retaining a medicament store; and a dose counter, the dose counter having a moveable actuator and a chassis mounted on the body; the chassis being heat staked in position on the body. This is be highly advantageous in that the chassis can be very accurately positioned and held firmly in place, thereby further improving counting accuracy compared to prior art arrangements in which some movement of the chassis relative to the body may be tolerated in snap-fit connections.

The chassis may have at least one of a pin or aperture heat staked to a respective aperture or pin of the body.

The chassis may have a ratchet counter output member mounted thereon.

The ratchet counter output member may comprise a ratchet wheel arranged to reel in incrementally a dose meter tape having a dosage indicia located thereon.

According to a further aspect of the present invention there is provided a method of assembling an inhaler including the step of heat staking the chassis onto the body. The step of heat staking is highly advantageous in fixedly positioning the chassis onto the body in order to achieve highly accurate dose counting in the assembled inhaler.

The method of assembly may include mounting a spring-returned ratchet actuator in the body before heat staking the chassis in place. The method of assembly may include pre-assembling the chassis with a dose meter tape prior to the step of heat staking the chassis in place. The method of assembly may include attaching a dose meter cover onto the body after the heat staking step. The cover may be welded onto the body or may in some embodiments be glued or otherwise attached in place.

According to a further aspect of the present invention there is provided an inhaler for inhaling medicament and having a body, the body have a main part thereof for retaining a medicament store; and a dose counter, the dose counter being located in a dose counter chamber of the body which is separated from the main part of the body, the dose counter chamber of the body having a dosage display and being perforated so as to permit the evaporation of water or aqueous matter in the dose counter chamber into the atmosphere.

This is high advantageous since it enables the inhaler to be thoroughly washed and the dose counting chamber can thereafter dry out fully.

The display may comprise a mechanical counter display inside the dose counter chamber and a window for viewing the mechanical counter display. The mechanical counter display may comprise a tape. The perforated dose counter chamber may therefore enable reliable washing of the inhaler, if desired by the user, and may therefore dry out without the display window misting up.

The dose counter chamber may be perforated by a drain hole formed through an outer hole of the body. The drain hole may be located at a bottom portion of the body of the inhaler, thereby enabling full draining of the inhaler to be encouraged after washing when the inhaler is brought into an upright position.

According to a further aspect of the present invention there is provided a dose counter for an inhaler, the dose counter having a display tape arranged to be incrementally driven from a tape stock bobbin onto an incremental tape take-up drive shaft, the bobbin having an internal bore supported by and for rotation about a support shaft, at least one of the bore and support shaft having a protrusion which is resiliently biased into frictional engagement with the other of the bore and support shaft with longitudinally extending mutual frictional interaction. This arrangement may provide good friction for the bobbin, thereby improving tape counter display accuracy and preventing the bobbin from unwinding undesirably for example if the inhaler is accidentally dropped.

The support shaft may be forked and resilient for resiliently biasing the support shaft and bore into frictional engagement.

The support shaft may have two forks, or more in some cases, each having a radially extending protrusion having a friction edge extending therealong parallel to a longitudinal axis of the support shaft for frictionally engaging the bore of the support shaft with longitudinally extending frictional interaction therebetween.

The bore may be a smooth circularly cylindrical or substantially cylindrical bore.

Each of the above inhalers in accordance with aspects of the present invention may have a medicament canister mounted thereto.

The canister may comprise a pressurised metered dose canister having a reciprocally movable stem extending therefrom and movable into a main canister portion thereof for releasing a metered dose of medicament under pressure, for example by operating a metered dose valve inside the canister body. The canister may be operable by pressing by hand on the main canister body.

In cases in which one or more support rails or inner wall support formations are provided, the canister may at all times when within the canister chamber have a clearance of about 0.25 to 0.35 mm from the first inner wall support formation. The clearance may be almost exactly 0.3 mm. This clearance which may apply to the canister body itself or to the canister once a label has been applied, is enough to allow smooth motion of the canister in the inhaler while at the same time preventing substantial rocking of the canister which could result in inaccurate counting by a dose counter of the inhaler, especially when lower face of the canister is arranged to engage an actuator member of the dose counter for counting purposes.

According to a further aspect of the invention, a method of assembling a dose counter for an inhaler comprises the steps of providing a tape with dosing indicia thereon; providing tape positioning indicia on the tape; and stowing the tape while monitoring for the tape positioning indicia with a sensor. The method advantageously permits efficient and accurate stowing of the tape, e.g. by winding.

The dosing indicia may be provided as numbers, the tape positioning indicia may be provided as one or more lines across the tape. The stowing step comprises winding the tape onto a bobbin or shaft, and, optionally, stopping winding when the positioning indicia are in a predetermined position. The tape may be provided with pixelated indicia at a position spaced along the tape from the positioning indicia. The tape may also be provided with a priming dot.

According to a further aspect of the invention, a tape system for a dose counter for an inhaler has a main elongate tape structure, and dosing indicia and tape positioning indicia located on the tape structure. The tape positioning indicia may comprise at least one line extending across the tape structure. The tape system may comprise pixelated indicia located on the tape structure and spaced from the positioning indicia. The tape system may comprise a priming dot located on the tape structure. The positioning indicia may be located between the timing dot and the pixelated indicia. The main elongate tape structure may have at least one end thereof wound on a bobbin or shaft.

A further aspect of the invention provides a method of designing an incremental dose counter for an inhaler comprising the steps of calculating nominal canister fire and dose counter positions for a dose counter actuator of the inhaler; calculating a failure/success rate for dose counters built to tolerance levels for counting each fire of inhalers in which the dose counter actuators may be applied; and selecting a tolerance level to result in said failure/success rate to be at or below/above a predetermined value. This is highly advantageous in that it allows an efficient and accurate prediction of the reliability of a series of inhaler counters made in accordance with the design.

The method of designing may include selecting the failure/success rate as a failure rate of no more than one in 50 million. The method of designing may include setting an average count position for dose counters built to the tolerances to be at or after an average fire position thereof during canister firing motion. The method of designing may include setting the average count position to be about 0.4 to 0.6 mm after the average fire position, such as about 0.48 mm after. The method of designing may include setting tolerances for the standard deviation of the fire position in dose counters built to the tolerances to be about 0.12 to 0.16 mm, such as about 0.141 mm. The method of designing may include setting tolerances for the standard deviation of the count positions in dose counters built to the tolerances to be about 0.07 to 0.09 mm, such as about 0.08 mm. A further aspect of the invention provides a computer implemented method of designing an incremental dose counter for an inhaler which includes the aforementioned method of designing.

A further aspect of the invention provides a method of manufacturing in a production run a series of incremental dose counters for inhalers which comprises manufacturing the series of dose counters in accordance with the aforementioned method of designing.

A further aspect of the invention provides a method of manufacturing a series of incremental dose counters for inhalers, which comprises manufacturing the dose counters with nominal canister fire and dose count positions of a dose counter actuator relative to a dose counter chassis (or inhaler main body), and which includes building the dose counters with the average dose count position in the series being, in canister fire process, at or after the average canister fire position in the series.

According to a further aspect of the invention, the method provides fitting each dose counter in the series of incremental dose counters to a corresponding main body of an inhaler.

These aspects advantageously provide for the production run of a series of inhalers and dose counters which count reliably in operation.

According to a further aspect of the invention, an incremental dose counter for a metered dose inhaler has a body arranged to retain a canister for movement of the canister relative thereto, the incremental dose counter having a main body, an actuator arranged to be driven and to drive an incremental output member in a count direction in response to canister motion, the actuator being configured to restrict motion of the output member in a direction opposite to the count direction. This advantageously enables an inhaler dose counter to keep a reliable count of remaining doses even if dropped or otherwise jolted.

The output member may comprise a ratchet wheel. The actuator may comprise a pawl and in which the ratchet wheel and pawl are arranged to permit only one-way ratcheting motion of the wheel relative to the pawl. The dose counter may include an anti-back drive member fixed to the main body. In a rest position of the dose counter, the ratchet wheel is capable of adopting a configuration in which a back surface of one tooth thereof engages the anti-back drive member and the pawl is spaced from an adjacent back surface of another tooth of the ratchet wheel without positive drive/blocking engagement between the pawl and wheel.

BRIEF DESCRIPTION OF THE DRAWINGS

The present invention may be carried out in various ways and preferred embodiment of a dose counter, inhaler and methods of assembly, design and manufacture will now be described with reference to the accompanying drawings in which:

FIGS. 6A, 6B, 6C, 6D, 6E, 6F, 6G and 6H are various views of dose counter components of the inhaler;

FIGS. 7A and 7B are sectional views showing canister clearance inside the main body of the inhaler;

FIG. 7C is a further sectional view similar to that of FIG. 7B but with the canister removed;

FIG. 7D is a top plan view of the inhaler main body;

FIGS. 8A, 8B, 8C and 8D show the inhaler main body and dose counter components during assembly thereof;

FIG. 12 is an enlarged version of part of FIG. 4A;

FIG. 13 shows an end portion of a tape of the dose counter;

DETAILED DESCRIPTION OF THE INVENTION

Figure 1:
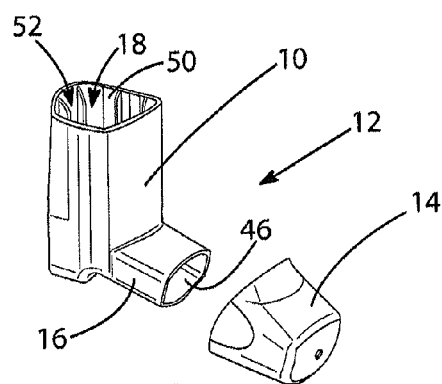
FIG. 1 is an isometric view of a main body of an embodiment of an inhaler related to the invention together with a mouthpiece cap therefor.
Figure 2:
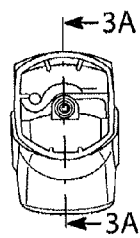
FIG. 2 is a top plan view of the components as shown in FIG. 1.
Figure 3A:
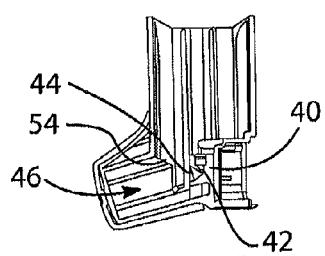
FIG. 3A is a section on the plane 3A-3A in FIG. 2.
Figure 3B:
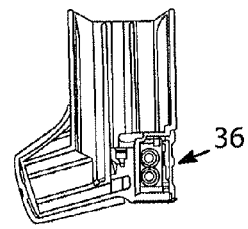
FIG. 3B is a view corresponding to FIG. 3A but with a dose counter fitted to the main body of the inhaler.

FIG. 1 shows a main body 10 of a manually operated metered dose inhaler 12 in accordance with an embodiment related to the present invention and having a mouthpiece cap 14 securable over a mouthpiece 16 of the main body.

The main body has a canister chamber 18 into which a canister 20 (FIG. 7A) is slideable. The canister 20 has a generally cylindrical main side wall 24, joined by a tapered section 26 to a head portion 28 having a substantially flat lower face 30 which has an outer annular drive surface 32 arranged to engage upon and drive an actuation pin 34 of a dose counter 36 as will be described. Extending centrally and axially from the lower face 30 is a valve stem 38 which is arranged to sealingly engage in a valve stem block 40 of the main body 10 of the inhaler 12. The valve stem block 40 has a passageway 42 leading to a nozzle 44 for directing the contents of the canister 20, namely active drug and propellant, towards an air outlet 46 of the inhaler main body 12. It will be appreciated that due to gaps 48 between the canister 20 and an inner wall 50 of the main body 10 of the inhaler 12 an open top 52 of the main body 10 forms an air inlet into the inhaler 12 communicating via air passageway 54 with the air outlet 46, such that canister contents exiting nozzle 44 mix with air being sucked by the user through the air passageway 54 in order to pass together through the air outlet and into the mouth of the user (not shown).

Figure 4B:
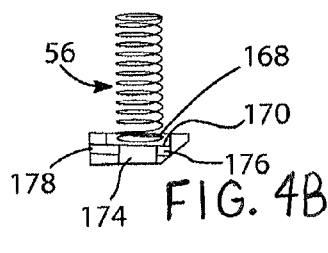
FIG. 4B is a view in the direction 4B in FIG. 4C of a spring retainer of the dose counter.
Figure 4C:
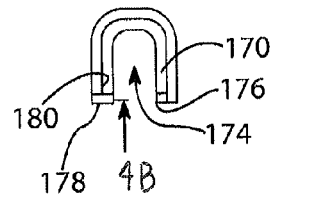
FIG. 4C is a top view of the spring retainer of FIG. 4B.
Figure 4A:
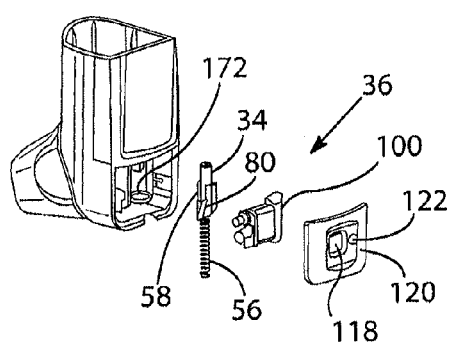
FIG. 4A is an exploded view of the inhaler main body, mouthpiece cap, dose counter and a dose counter window.

The dose counter 36 will now be described. The dose counter 36 includes an actuation pin 34 biased upwardly from underneath by a return spring 56 once installed in the main body 10. As best shown in FIGS. 4A, 6H and 8A, the pin 34 has side surfaces 58, 60 arranged to slide between corresponding guide surfaces 62, 64 located in a dose counter chamber 66 of the main body 10, as well as an end stop surface 68 arranged to engage a corresponding end stop 70 formed in the dose counter chamber 66 to limit upward movement of the pin 34. The pin 34 has a top part 72 which is circularly cylindrical and extends through an aperture 74 formed through a separator wall 76 which separates the canister chamber 18 from the dose counter chamber 66. The top part 72 of the pin 34 has a flat top surface 78 which is arranged to engage the outer annular drive surface 32 of the canister 20.

The actuation pin 34 is integrally formed with a drive or actuator pawl 80. The actuator pawl 80 has a generally inverted U-shape configuration, having two mutually spaced and parallel arms 82, 84 extending from a base portion of the actuation pin 34, each holding at respective distal ends 88 thereof opposite ends of a pawl tooth member 90 which extends in a direction substantially perpendicular to the arms 82, 84, so as to provide what may be considered a "saddle" drive for pulling on each of the 11 drive teeth 92 of a ratchet wheel 94 of an incremental drive system 96 or ratchet mechanism 96 of the dose counter 36. As shown for example in FIG. 10B, the pawl tooth member 90 has a sharp lower longitudinal side edge 98 arranged to engage the drive teeth 92, the edge-to-surface contact provided by this engagement providing very accurate positioning of the actuator pawl 80 and resultant rotational positioning of the ratchet wheel 94.

Figure 6A:
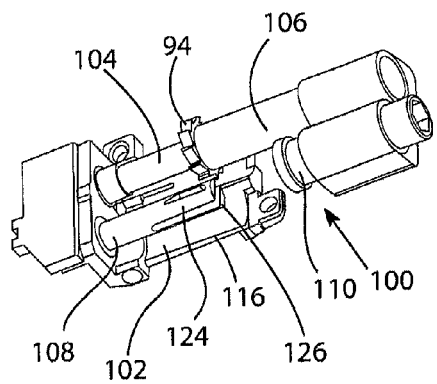

The dose counter 36 also has a chassis preassembly 100 which, as shown in FIGS. 4A and 6A, includes a chassis 102 having a first shaft 104 receiving the ratchet wheel 94 which is secured to a tape reel shaft 106, and a second shaft (or split pin) 108 which is parallel to and spaced from the first shaft 104 and which slidably and rotationally receives a tape stock bobbin 110.

Figure 6B:
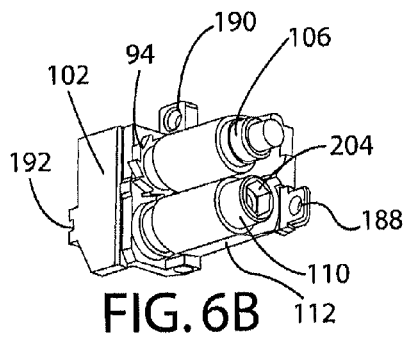
Figure 6C:
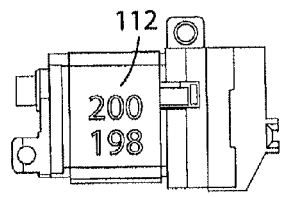

As shown in FIG. 6B, when the inhaler has not been used at all, the majority of a tape 112 is wound on the tape stock bobbin 110 and the tape 112 has a series of regularly spaced numbers 114 displayed therealong to indicate a number of remaining doses in the canister 20. As the inhaler is repeatedly used, the ratchet wheel 94 is rotated by the actuator pawl 80 due to operation of the actuation pin 34 by the canister 20 and the tape 112 is incrementally and gradually wound on to the tape reel shaft 106 from the second shaft 108. The tape 112 passes around a tape guide 116 of the chassis 102 enabling the numbers 114 to be displayed via a window 118 in a dose counter chamber cover 120 having a dose marker 132 formed or otherwise located thereon.

Figure 6D:
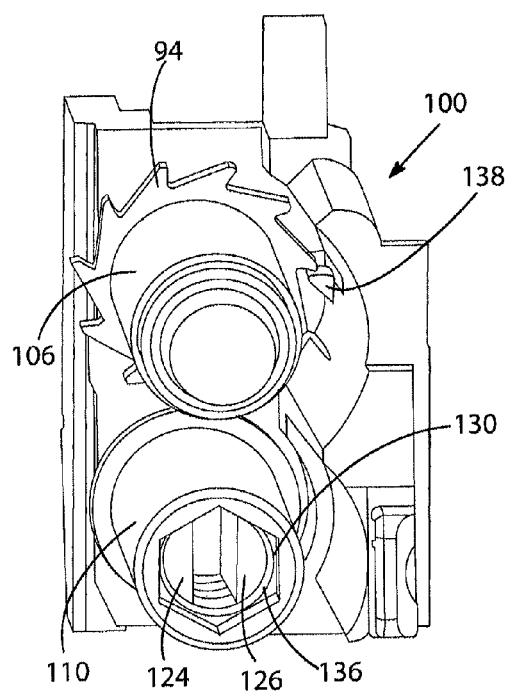
Figure 6E:
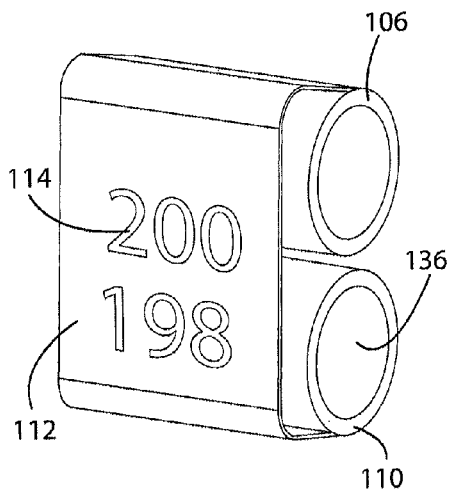

As shown in FIGS. 6A and 6D, the second shaft 108 is forked with two forks 124, 126. The forks 124, 126 are biased away from one another. The forks have located thereon at diametrically opposed positions on the second shaft 108 friction or control elements 128, 130, one on each fork. Each control element extends longitudinally along its respective fork 124, 126 and has a longitudinally extending friction surface 132, 134 which extends substantially parallel to a longitudinal axis of the second shaft and is adapted to engage inside a substantially cylindrical bore 136 inside the tape stock bobbin 110. This control arrangement provided between the bore 136 and the control elements 128, 130 provides good rotational control for the tape stock bobbin 110 such that it does not unwind undesirably such as when the inhaler is dropped. The tape force required to unwind the tape stock bobbin 110 and overcome this friction force is approximately 0.1 N.

As can be seen in FIG. 6D, as well as FIGS. 6G and 10A to 10F, the chassis 102 is provided with an anti-back drive tooth 138 or count pawl 138 which is resiliently and substantially fixedly mounted thereto. As will be described below and as can be seen in FIGS. 10A to 10F, when the actuation pin 34 is depressed fully so as to fire the metered valve (not shown) inside the canister 20, the actuator pawl 80 pulls down on one of the teeth 92 of the ratchet wheel 94 and rotates the wheel 94 anticlockwise as shown in FIG. 6D so as to jump one tooth 92 past the count pawl 138, thereby winding the tape 112 a distance incrementally relative to the dose marker 122 on the dose counter chamber 120 so as to indicate that one dose has been used.

Figure 9:
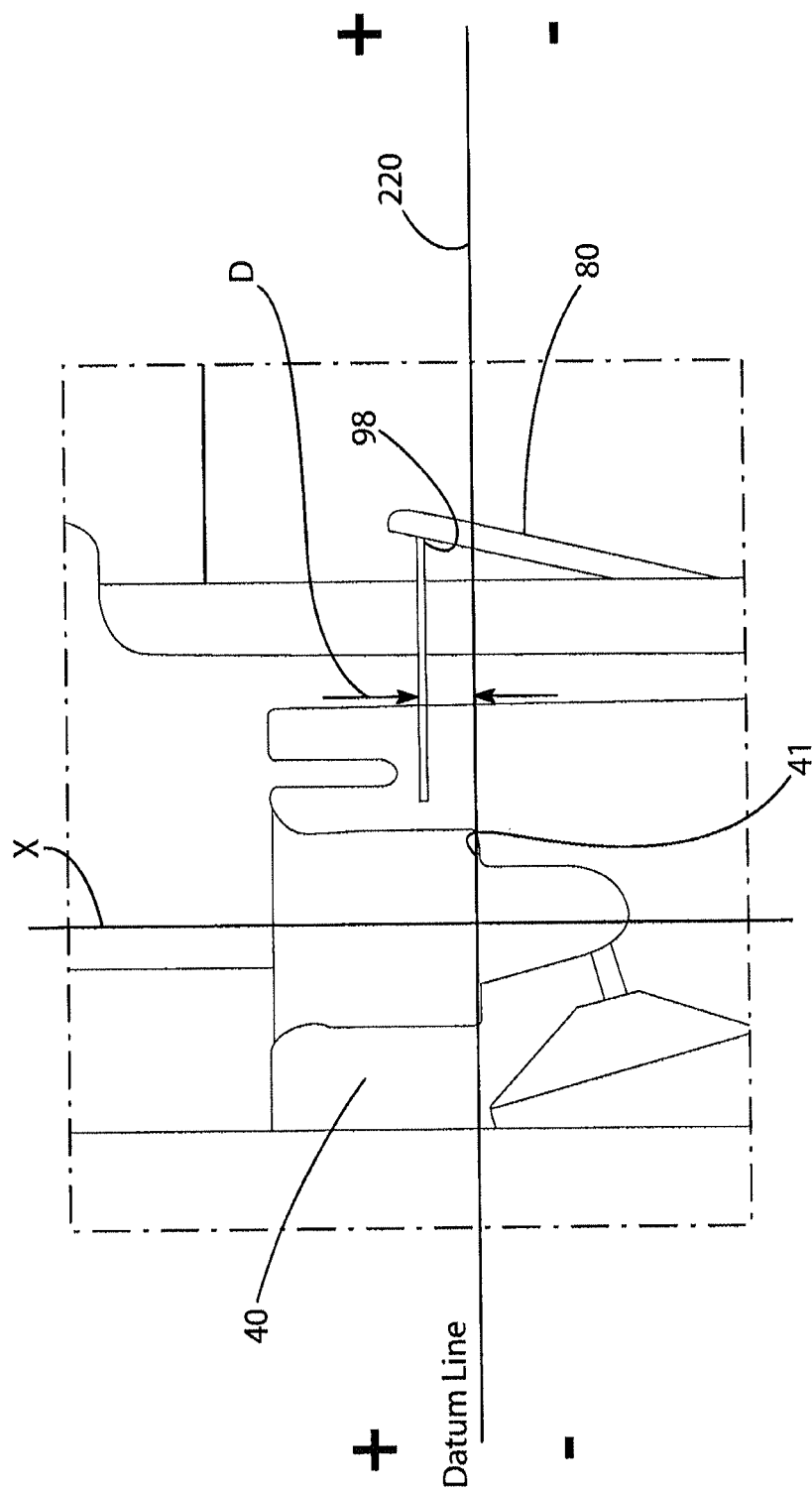
FIG. 9 shows a sectional side view of a datum line for an actuator pawl of the dose counter.
Figure 10A:
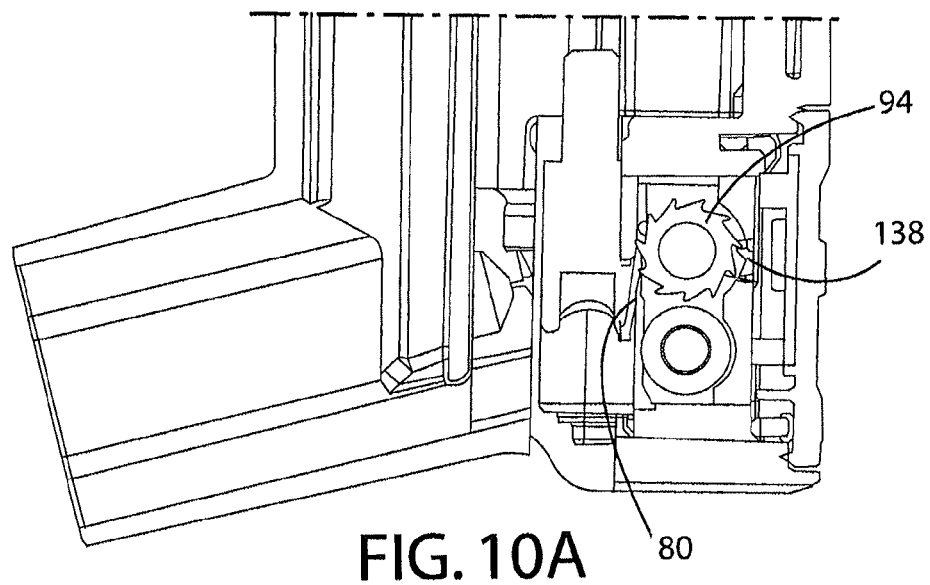
FIGS. 10A, 10B, 10C, 10D, 10E and 10F show various side views of positions and configurations of the actuator pawl, a ratchet wheel, and a count pawl.
Figure 10B:
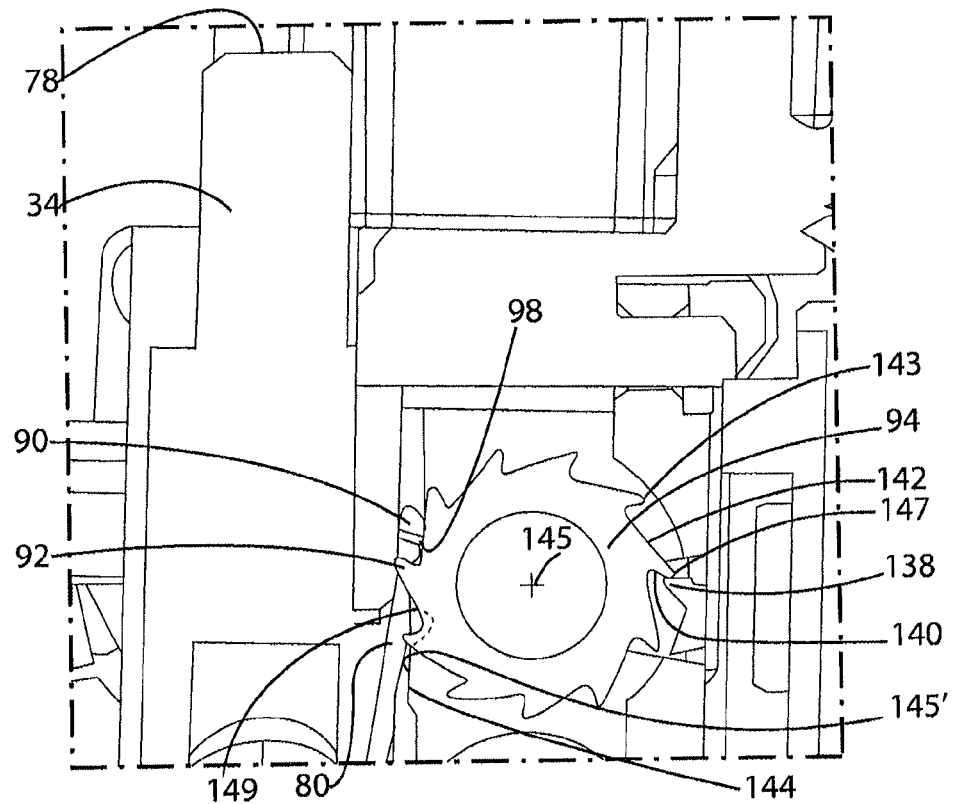

With reference to FIG. 10B, the teeth of the ratchet wheel 94 have tips 143 which are radiused with a 0.1 mm radius between the flat surfaces 140, 142. The ratchet wheel 94 has a central axis 145 which is 0.11 mm above datum plane 220 (FIG. 9). A top/nose surface 147 of the anti-back drive tooth 138 is located 0.36 mm above the datum plane 220. The distance vertically (i.e. transverse to datum plane 220—FIG. 9) between the top nose surface 147 of the anti-back drive tooth is 0.25 mm from the central axis 145 of the wheel 94. Bump surface 144 has a lateral extent of 0.20 mm, with a vertical length of a flat 145' thereof being 1 mm, the width of the bump surface being 1.22 mm (in the direction of the axis 145), the top 149 of the bump surface 144 being 3.02 mm vertically below the axis 145, and the flat 145' being spaced a distance sideways (i.e. parallel to the datum plane 220) 2.48 mm from the axis 145. The top surface 78 of the pin 34 (FIG. 6H) is 11.20 mm above the datum plane 220 (FIG. 9) when the actuator pawl 80 and pin 34 are in the start configuration. The length of the valve stem 22 is 11.39 mm and the drive surface 32 of the canister 20 is 11.39 mm above the datum plane 220 when the canister is at rest waiting to be actuated, such that there is a clearance of 0.19 mm between the canister 20 and the pin 34 in this configuration.

FIGS. 10A and 10B show the actuator pawl 80 and ratchet wheel 94 and count pawl 138 in a start position in which the flat top 78 of the pin 34 has not yet been engaged by the outer annular drive surface 32 of the canister 20 or at least has not been pushed down during a canister depression.

In this "start" position, the count pawl 138 engages on a non-return back surface 140 of one of the teeth 92 of the ratchet wheel 94. The lower side edge 98 of the actuator pawl is a distance "D" (FIG. 9) 1.33 mm above datum plane 220 which passes through bottom surface or shoulder 41 of valve stem block 40, the datum plane 220 being perpendicular to a main axis "X" of the main body 10 of the inhaler 12 which is coaxial with the centre of the valve stem block bore 43 and parallel to a direction of sliding of the canister 20 in the main body 10 of the inhaler 12 when the canister is fired.

As shown in FIG. 10B, an advantageous feature of the construction is that the pawl tooth/actuator 90 acts as a supplementary anti-back drive member when the inhaler 12 is not being used for inhalation. In particular, if the inhaler 12 is accidentally dropped, resulting in a jolt to the dose counter 36 then, if the wheel 94 would try to rotate clockwise (backwards) as shown in FIG. 10B, the back surface 140 of a tooth will engage and be blocked by the tooth member 90 of the pawl 80. Therefore, even if the anti-back drive tooth 138 is temporarily bent or overcome by such a jolt, undesirable backwards rotation of the wheel 94 is prevented and, upon the next canister firing sequence, the pawl 90 will force the wheel 94 to catch up to its correct position so that the dose counter 36 continues to provide correct dosage indication.

Figure 10E:
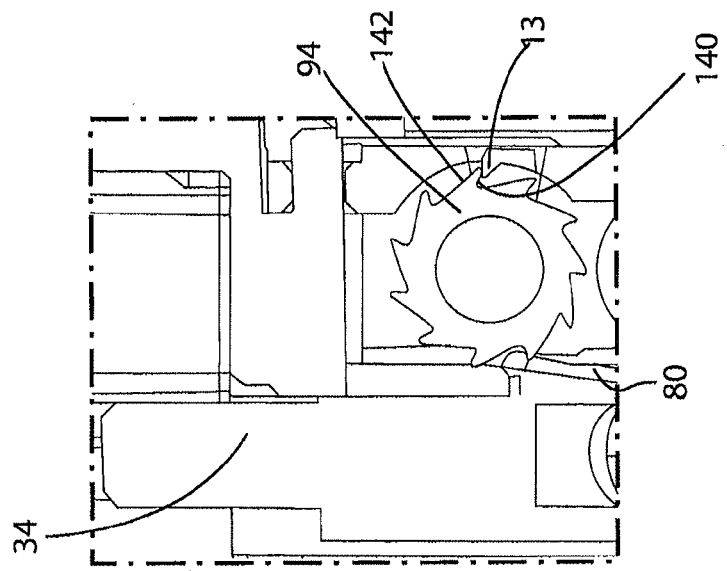
Figure 10C:
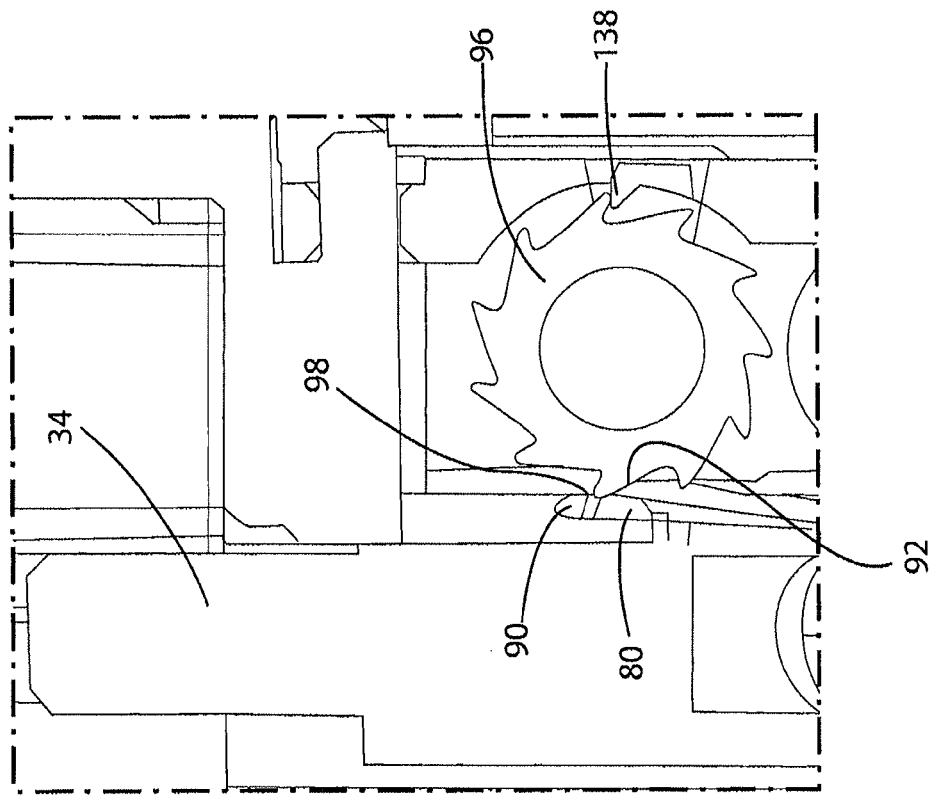

FIG. 10C shows a configuration in which the actuator pawl 80 has been depressed with the pin 34 by the canister 20 to a position in which the side edge 98 of the pawl tooth member 90 is just engaged with one of the teeth 92 and will therefore upon any further depression of the pin 34 begin to rotate the wheel 94. This is referred to as a "Reset" position or configuration. In this configuration, the lower side edge 98 of the actuator 80 is 0.64 mm above the datum plane 220.

Figure 10F:
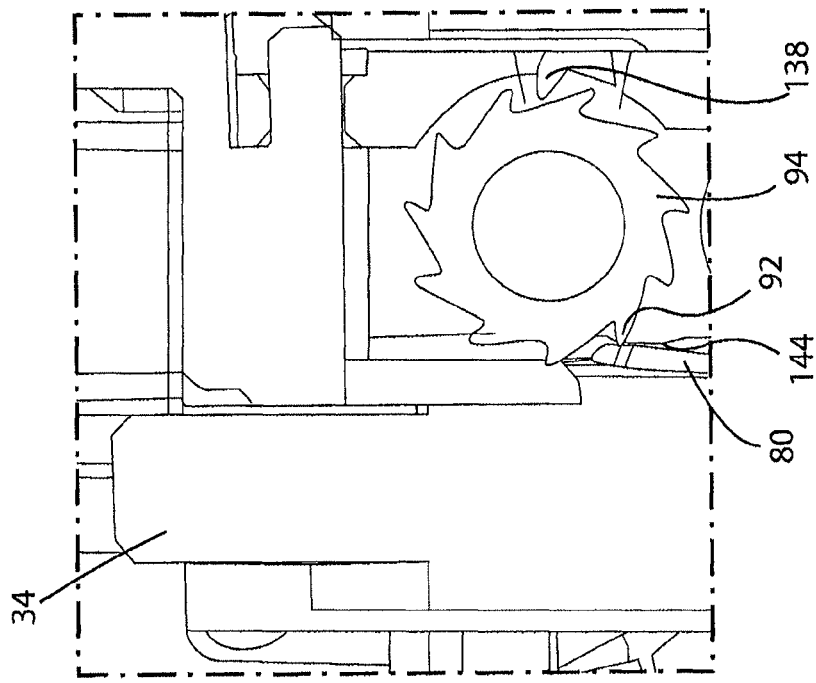
Figure 10D:
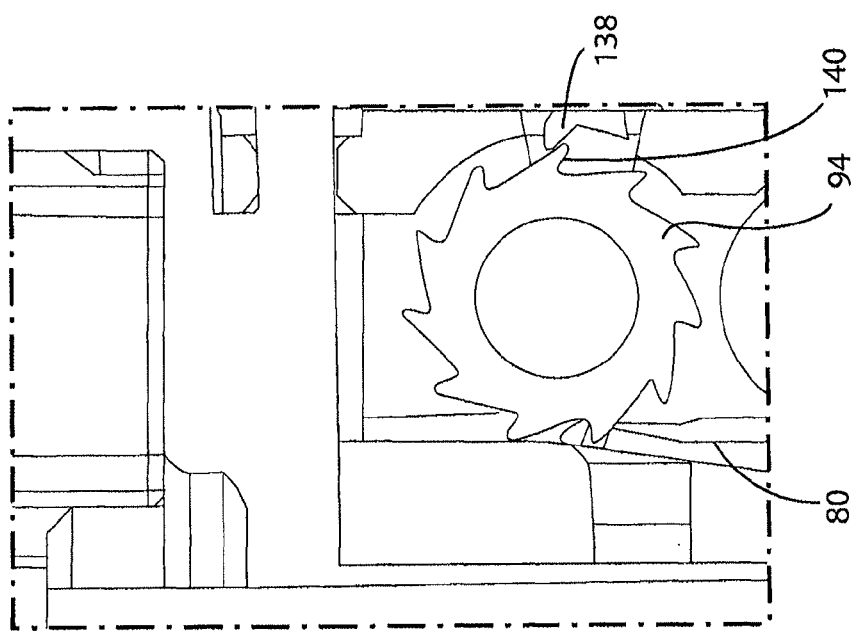

FIG. 10D shows a configuration in which the actuator pawl 80 has been moved to a position lower than that shown in FIG. 10C and in which the metered dose valve (not shown) inside the canister has at this very position fired in order to eject active drug and propellant through the nozzle 44. It will be noted that in this configuration the count pawl 138 is very slightly spaced from the back surface 140 of the same tooth 92 that it was engaging in the configuration of FIG. 10D. The configuration shown in FIG. 10D is known as a "Fire" configuration. In this configuration the lower side edge 98 of the actuator 80 is 0.47 mm below the datum plane 220.

FIG. 10E shows a further step in the sequence, called a "Count" position in which the actuator pawl 80 has rotated the ratchet wheel 94 by the distance circumferentially angularly between two of the teeth 92, such that the count pawl 138 has just finished riding along a forward surface 142 of one of the teeth 92 and has resiliently jumped over the tooth into engagement with the back surface 140 of the next tooth. Accordingly, in this "Count" configuration, a sufficiently long stroke movement of the pin 34 has occurred that the tape 112 of the dose counter 36 will just have counted down one dose. In this configuration, the lower side edge 98 of the actuator is 0.95 mm below the datum plane 220. Accordingly, in this position, the actuator 80 generally, including edge 98, is 0.48 mm lower than in the fire configuration. It has been found that, although the count configuration happens further on than the fire configuration, counting is highly reliable, with less than one in 50 failed counts per million. This is at least partially due to momentum effects and to the canister releasing some back pressure on the user in some embodiments as its internal metering valve fires.

In the configuration of FIG. 10F, the pawl 80 has been further depressed with the pin 34 by the canister 20 to a position in which it is just disengaging from one of the teeth 92 and the actuator pawl 80 is assisted in this disengagement by engagement of one of the arms 84 with a bump surface 144 on the chassis 102 (see FIG. 6G) and it will be seen at this point of disengagement, which is called an "End" configuration, the count pawl 138 is positioned exactly halfway or substantially halfway between two of the drive teeth 92. This advantageously means therefore that there is a minimum chance of any double counting or non-counting, which would be undesirable. In the end configuration, the side edge 98 of the actuator is 1.65 mm below the datum plane 220. It will be appreciated that any further depression of the actuator pawl 80 and pin 34 past the "End" configuration shown in FIG. 10F will have no effect on the position of the tape 112 displayed by the dose counter 36 since the actuator pawl 80 is disengaged from the ratchet wheel 94 when it is below the position shown in FIG. 10F.

As shown in FIGS. 7C and 7D, the inner wall 50 of the main body 10 is provided with a two-step support rail 144 which extends longitudinally along inside the main body and is located directly adjacent the aperture 74. As shown in FIG. 7B a diametrically opposed two-step support rail 146 is also provided and this diametrically opposed in the sense that a vertical plane (not shown) can pass substantially directly through the first rail 144, the aperture 74, a central aperture 148 of the valve stem block 40 (in which canister stem 25 is located) and the second two-step support rail 146. As shown in FIG. 7A and schematically in FIG. 7B, the rails 144, 146 provide a maximum clearance between the canister 20 and the rails 144, 146 in a radial direction of almost exactly 0.3 mm, about 0.25 to 0.35 mm being a typical range. This clearance in this plane means that the canister 20 can only rock backwards and forwards in this plane towards away from the actuation pin 34. A relatively small distance and this therefore prevents the canister wobbling and changing the height of the actuation pin 34 a as to undesirably alter the accuracy of the dose counter 36. This is therefore highly advantageous.

The inner wall 50 of the main body 10 is provided with two further two-step rails 150 as well as two pairs 152, 154 of rails extending different constant radial amounts inwardly from the inner wall 50, so as to generally achieve a maximum clearance of almost exactly 0.3 mm around the canister 20 for all of the rails 144, 146, 150, 152, 154 spaced around the periphery of the inner wall 50, in order to prevent undue rocking while still allowing canister motion freely inside the inhaler 12. It will be clear from FIG. 7C for example that the two-step rails have a first portion near an outlet end 156 of the canister chamber 18, the first portion having a substantially constant radial or inwardly-extending width, a first step 160 leading to a second portion 162 of the rail, the second portion 102 having a lesser radial or inwardly extending extent than the first portion 156, and finally a second step 164 at which the rail merges into the main inner wall 50 main surface.

A method of assembling the inhaler 12 will now be described.

With reference to FIG. 8A, the main body 10 of the inhaler 12 is formed by two or more plastics mouldings which have been joined together to the configuration shown.

As shown in FIG. 8B, the actuator pawl 80 and pin 34 are translated forward into position into a pin receiving area 166 in the dose counter chamber 66 and the pin 34 and actuator 80 may then be raised until the pin 34 emerges through the aperture 74.

Next, the return spring 56 may be inserted below the pin 34 and a generally cylindrical annular lower end 168 of the spring 56 may be moved by a tweezer or tweezer-like assembly tool (not shown) into engagement with a shelf 170 of a spring retainer 172 in the dose counter chamber 66. The spring retainer 172 is U-shaped and the shelf 170 is U-shaped and has a recess 174 formed below it. As shown in FIGS. 4B, 4C and 12 shelf 170 includes three chamfer surfaces 176, 178, 180 arranged to assist in moving the lower end of the spring 168 into position onto the shelf using the assembly tool (not shown). Once the lower end of the spring 168 is in place, the assembly tool (not shown) can easily be removed at least partly via the recess 174 below the lower end 168 of the spring 56.

The tape 112 is attached at one end (not shown) to the tape stock bobbin 110 and is wound onto the bobbin by a motor 200 (FIG. 13) having a hexagonal output shaft 202 which engages in a hexagonal socket 204 (FIG. 6B) of the bobbin. During winding, the tape is monitored by a sensor 206, which may be in the form of a camera or laser scanner, which feeds data to a computer controller 205 for the motor 200. The controller 205 recognises three positioning markers 210 in the form of lines across the tape 112 and stops the motor 202 when the tape 112 is nearly fully wound onto the bobbin 110, such that the distal end 212 of the tape 112 can be secured, e.g. by adhesive, to the tape reel shaft 106. The controller 205 also recognises a pixelated tape size marker 214 observed by the sensor 206 and logs in a stocking system data store 217 details of the tape 112 such as the number of numbers 114 on the tape, such as one hundred and twenty or two hundred numbers 114. Next, the tape reel shaft is wound until an appropriate position of the lines 210 at which a priming dot 216 will, once the bobbin 110 and reel shaft 106 are slid onto the second shaft 108 and second shaft 104, be in a position to be located in the window 118 when the inhaler 12 is fully assembled. In the embodiments, the bobbin 110 and reel shaft 106 may be slid onto the shafts 108, 104 before the tape 112 is secured to the reel shaft 106 and the reel shaft may then be wound to position the priming dot 216.

Next, the assembled dose counter components of the chassis preassembly 100 shown in FIG. 6B may as shown in FIG. 8C be inserted into the dose counter chamber 66, with pins 182, 184, 186 formed on the main body 10 in the dose counter chamber 66 passing through apertures or slots 188, 190, 192 formed on the chassis 102, such that the pins 182, 184, 186 extend through (or at least into) the apertures or slots 188, 190, 192. With the chassis 102 being relatively firmly pushed towards the main body 10, the pins 182, 184, 186 are then heat staked and the chassis 102 is therefore after this held very firmly in position in the main body and is unable to move, thereby assisting in providing great accuracy for the dose counter 36. Next, as shown in FIG. 8D, the dose counter chamber cover 120 may be fitted over the dose counter chamber 66 and may be secured in place such as by welding, with the priming dot 216 being displayed through the window.

The user can, when readying the inhaler 12 for first use, prime the inhaler by depressing the canister 20 three times which will bring the first number 114 on the tape into display through the window 118 in place of the priming dot 216, the number 114 shown in FIG. 8D being "200", thereby indicating that 200 doses are remaining to be dispensed from the canister 20 and inhaler 12.

Figure 5:
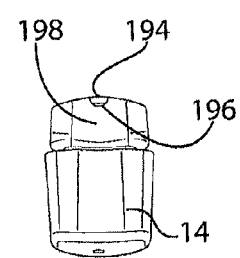
FIG. 5 is a bottom view of the assembled inhaler main body, mouthpiece cap, dose counter and dose counter window.

As shown in FIG. 8D, and in FIG. 5, an open drain hole 194 is provided at the bottom of the dose counter chamber 66 by a substantially semi-circular cut-out or recess formation 196 in a lower surface 198 of the main body 10 of the inhaler. Accordingly, if the user (not shown) should decide to wash the main body 10 of the inhaler, for example after encountering an unhygienic situation or simply as a matter of choice, the drain hole 194 allows initial draining of water from inside the dose counter chamber 66 and also thereafter evaporation of water or any aqueous matter in the dose counter chamber 66 so that the window 118 does not mist up undesirably.

Figure 11:
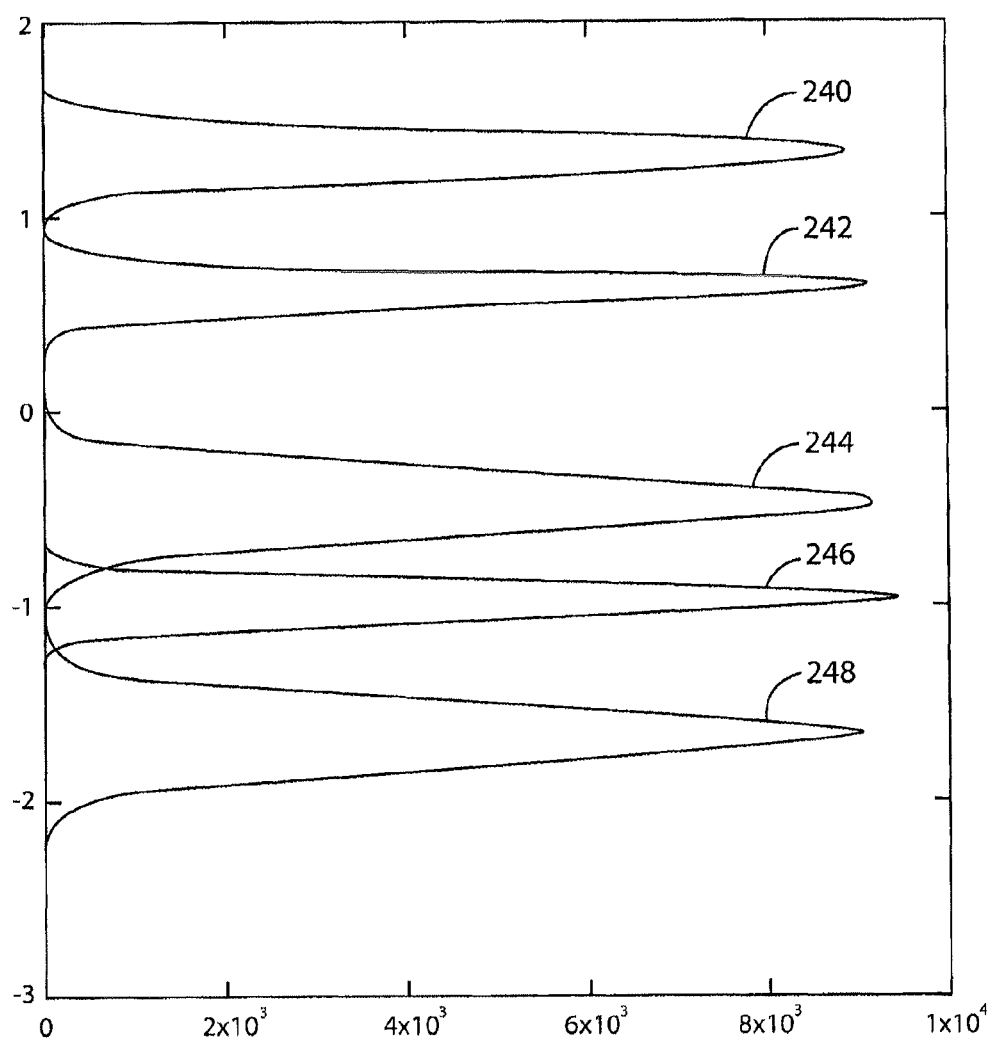
FIG. 11 shows distributions for tolerances of start, reset, fire, count and end positions for the actuator of the dose counter.
Figure 14:
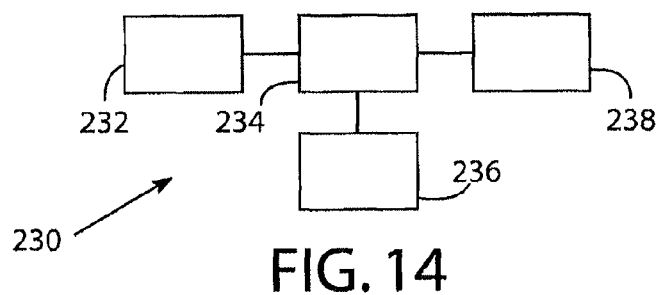
FIG. 14 shows a computer system for designing the dose counter.

FIG. 14 shows a computer system 230 for designing the dose counter 36 and in particular for calculating distributions representative of average positions and standard deviations in a production series of inhalers of the start, reset, fire, count and end positions of the actuator lower side edge 98 relative to the datum plane 220 (FIG. 9) and therefore of the actuator pawl 80 generally relative to the ratchet wheel 94, chassis 102 and, when the inhaler 12 is fully assembled, the main body 10 of the inhaler 12. The computer system 230 includes a data store 232, a CPU 234, an input device 236 (such as a keyboard or communication port) and an output device 238 (such as a communications port, display screen and/or printer). A user may enter data via the input device 236 which may be used by the CPU 234 in a mathematical calculation to predict count failure rates when the various dose counters are to be built in a series with dose counter positions set with given averages and standard deviations and taking into account any momentum/inertia effects and metering valve user-back-pressure reduction effect which will occur upon canister firing of a given type of canister. The computer system 230 is thus mathematically used to design the distributions. For the inhaler 12 described herein with the dose counter 36 and canister 20, the distributions are designed as shown in FIG. 11. The x axis shows distance of the lower side surface 98 of the actuator 80 above the datum plane 220 and the y axis is representative of the distribution. Thus, curve 240 shows that the start configuration has an average 1.33 mm above the datum plane 200 (standard deviation is 0.1 mm), curve 242 shows that the reset configuration has an average of 0.64 mm above the datum plane 220 (standard deviation is 0.082 mm), curve 244 shows the fire configuration has an average 0.47 mm below the datum plane 220 (standard deviation is 0.141 mm), curve 246 shows the count configuration has an average 0.95 mm below the datum plane 220 (standard deviation is 0.080 mm), and curve 248 shows the end configuration has an average of 1.65 mm below the datum plane 220 (standard deviation is 0.144 mm).

FIGS. 15 to 20 show a version of the inhaler modified in accordance with the present invention. In these drawings, the same reference numerals have been used to those in the earlier drawings to denote the equivalent components. The inhaler 12 is the same as that in FIGS. 1 to 14 apart from the following modifications.

First, it can be seen that there is a modification in that the drive teeth 92 of the ratchet wheel 94 have a different profile to that in FIGS. 1 to 14. There are also only nine ratchet teeth 94 in this embodiment instead of eleven.

Figure 6F:
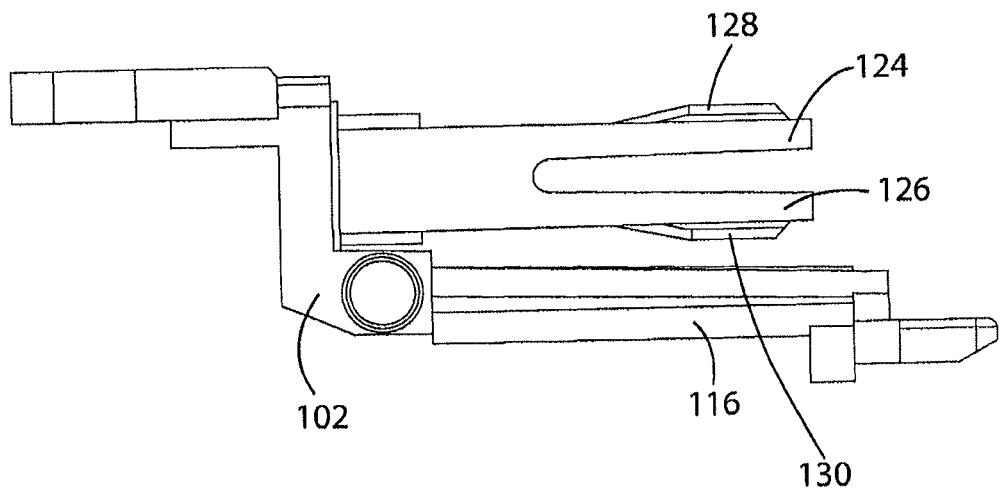
Figure 6G:
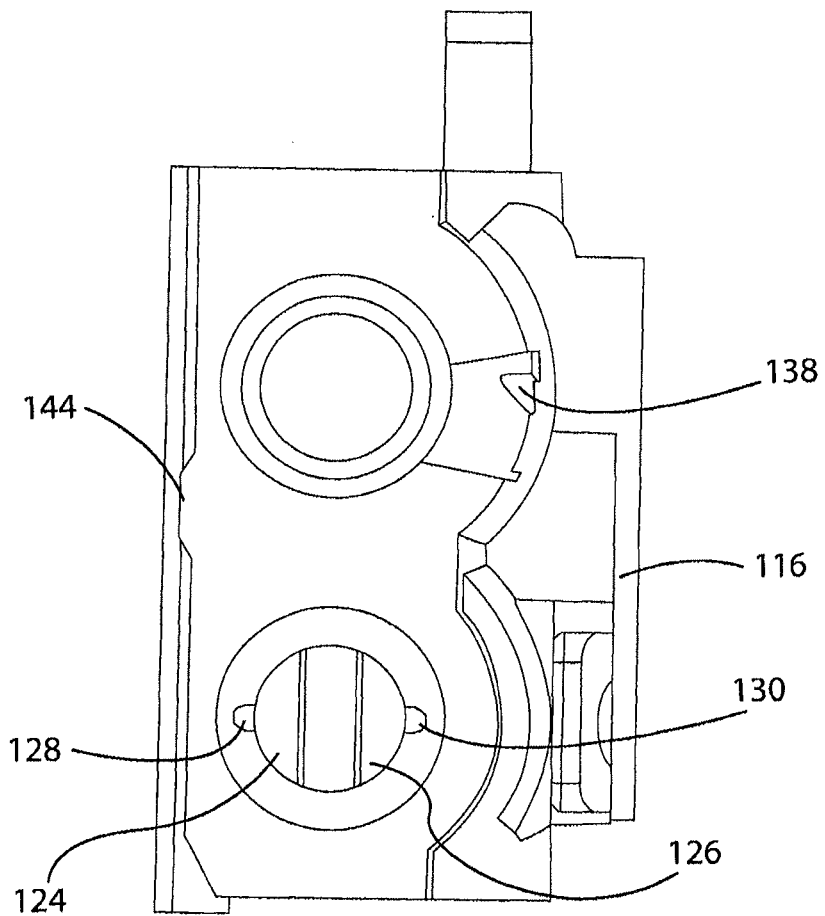
Figure 18A:
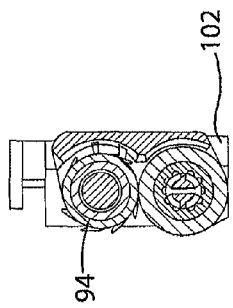
FIGS. 18A to 18C are views of the stock bobbin of FIGS. 15 to 17 mounted in the dose counter chassis of FIGS. 1 to 14, with the control elements of the forks of the second shaft (or split pin) having a profile slightly different to that in FIG. 6F, with the forks in a compressed configuration.
Figure 18B:
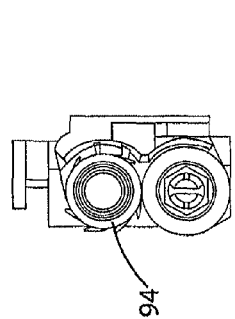
Figure 18C:
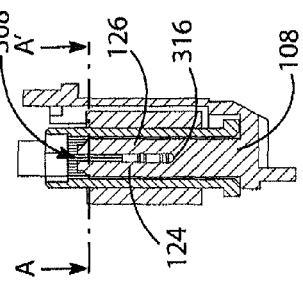
Figure 19A:
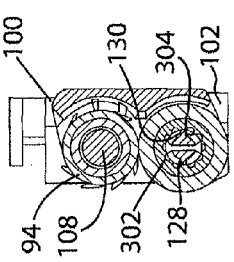
FIGS. 19A to 19C are views equivalent to FIGS. 18A to 18C but with the forks in a more expanded configuration due to a different rotational position of the stock bobbin.
Figure 19B:
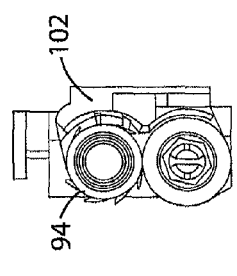
Figure 19C:
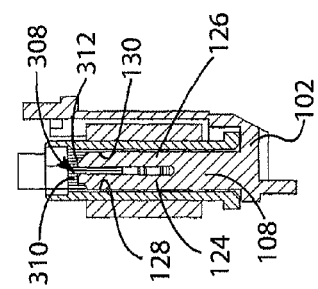

Additionally, as shown in FIGS. 18C and 19C, the control elements 128, 130 on the forks 124, 126 of the second shaft 108 have a tapered profile which is different to the profile of the control elements 128, 130 shown in FIG. 6F. Either profile can be used in the embodiment of FIGS. 15 to 20 however.

Figure 15:
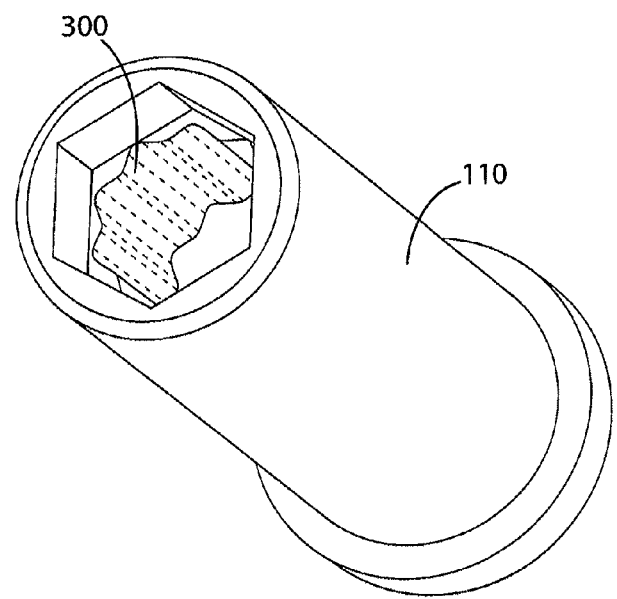
FIG. 15 is an isometric view of a stock bobbin modified in accordance with the present invention for use in the dose counter of the inhaler of FIGS. 1 to 14.

Furthermore, as shown in FIG. 15, the tape stock bobbin 110 has an inwardly facing generally cylindrical engagement surface 300 with a wavelike form extending partially therealong. The engagement surface 300 has a cross-section 301 perpendicular to the longitudinal length of the stock bobbin 110 which is constant therealong. This cross-section 301 can be seen in FIG. 16 and consists of a series of ten regularly spaced concavities 302 and ten convex wall portions 304. The convex wall portions 304 are equi-spaced between the concavities 302. Each concavity 302 has a radius of 0.2 mm. Each convex wall portion 304 also has a radius of 0.2 mm. Finally, the cross section 301 also includes flat wall portions 306 between all of the radiused wall portions of the concavities 302 and convex wall portions 304. The geometry of the cross-section 301 is therefore defined by the radii of the concavities 302 and convex wall portions 304, the flat wall portions 306 and the fact that there are ten concavities 302 and convex wall portions 304.

The minor diameter of the engagement surface 300, i.e. between the tips of opposite convex wall portions 304, is 2.46 mm. The major diameter of the engagement surface 300, i.e. between the outermost portions of the concavities 302, is 2.70 mm. The undeformed tip to tip maximum diameter of the forks 124, 126 of the split pin (the second shaft) 108, i.e. in the region of the maximum radio extent of the control elements 128, 130, is 3.1 millimeters and it will therefore be appreciated that the forks 124, 126 are resiliently compressed once the stock bobbin 110 has been assembled onto the split pin 108 in all rotational configurations of the stock bobbin 110 relative to the split pin 108. The minimum gap between the forks 124, 126 in the plane of the cross sections of FIGS. 18C and 19C is 1 mm when the split pin 108 is in the undeformed, pre-inserted state. When the split pin 108 is at maximum compression, as shown in FIGS. 18A to 18C when the control elements 128, 130 are shown to be engaged on top of the convex wall portions 304, the gap 308 between the tips 310, 312 of the forks 124, 126 is 0.36 mm. On the other hand, when the split pin 108 is at minimum compression (once inserted into the stock bobbin) as shown in FIGS. 19A to 19C, when the control elements 128, 130 rest in the concavities 302, the gap between the tips 310, 312 of the forks 124, 126 is 0.6 mm. The control elements 128, 130 are outwardly radiused with a radius also of 0.2 mm such that they can just rest on the concavities 302 with full surface contact (at least at an axial location on the split pin where the tapered control elements are at their maximum radial extent), without rattling in, locking onto or failing to fit in the concavities 302. The radii of the control elements 128, 130 is therefore preferably substantially the same as the radii of the concavities 302

It will be appreciated that whereas FIGS. 18B and 19B are end views along the coaxial axis of the stock bobbin 110 and split pin 108, FIGS. 18A and 19A are cross-sections. FIG. 19A is a section on the plane A-A' in FIG. 19C and FIG. 18A is a section at the same plane, but of course with the stock bobbin 110 rotated relative to the split pin 108.

As the inhaler 12 is used and the ratchet wheel 94 rotates in order to count used doses, the stock bobbin rotates incrementally through rotational positions in which rotation is resisted, i.e. due to increasing compression of the split pin 108 at such rotational positions, and rotational positions in which rotation is promoted, i.e. due to decreasing compression of the split pin 108 at such rotational positions and this may involve a click forward of the stock bobbin 110 to the next position equivalent to that in FIGS. 19A to 19C in which the control elements 128, 130 of the split pin art located in the concavities 302. This functionality firstly allows the stock bobbin to unwind during use as required, but also prevents the tape 112 from loosening during transit if the inhaler 12 is dropped, such as onto a hard surface. This is highly advantageous, since the tape 11 is prevented from moving to a position in which it will give an incorrect reading regarding the number of doses in the canister.

During compression and expansion of the forks in the radial direction between the two configurations shown in FIGS. 18C and 19C, the forks 124, 126 rotate about a point 316 on the split pin where the forks 124, 126 come together. This rotational action means that there is a camming action between the forks 124, 126 and the engagement surface 300 without significant friction but, nevertheless, the resilient forces provided by the regulator formed by the engagement surface 300 and forks 124, 126 are able to regulate unwinding of the tape such that it does not easily occur during transit or if the inhaler 12 is dropped. It has been found during testing that a force of 0.3 to 0.4 N needs to be applied to the tape 112 to overcome the regulator at the stock bobbin 110. 0.32 N is achieved with the control elements 128 having the profile shown in FIG. 19C and 0.38 N is achieved with the profile of the control elements 128 altered to be as shown as described with reference to FIG. 6F. These forces are substantially higher than the 0.1 N force mentioned above and undesirable movement of the tape is substantially avoided even if the inhaler is dropped onto a hard surface. The modified arrangement of FIGS. 15 to 20 does not provide this force "constantly" such that there is overall not an undesirably high friction of the tape 112 as it passes over the other components of the dose counter because, due to the incremental nature of the resilient forces at the regulator, the tape 112 can incrementally relax as it slides over the stationary chassis components.

Instead of having ten concavities 302 and convex wall portions 304, other numbers may be used, such as 8 or 12. However, it is preferred to have an even number, especially since two control elements 128, 130 are provided, so that all of the control elements 128, 130 will expand and contract simultaneously. However, other arrangements are envisaged with 3 or more forks and the number of concavities/convex wall portions may be maintained as an integer divisible by the number of forks to maintain a system with simultaneous expansion/contraction. For example, the use of 9, 12 or 15 concavities/convex wall portions with 3 forks is envisaged.

Instead of having the engagement surface 300 on the inside of the stock bobbin 110, it could be placed on the outside of the stock bobbin 110 so as to be engaged by flexible external legs/pawls or similar.

It will be noted that the regulator provided by the engagement surface 300 and forks 124, 126 does not only allow rotation of the stock bobbin in one direction as is the case with the ratchet wheel 94. Rotation in both directions is possible, i.e. forwards and backwards. This means that during assembly, the stock bobbin 110 can be wound backwards during or after fitting the bobbin 100, shaft 106 and tape 112 onto the carriage 102, if desired.

The stock bobbin 110 and the carriage 102 including the split pin 108 are both moulded of polypropylene material.

Figures 16, 20:
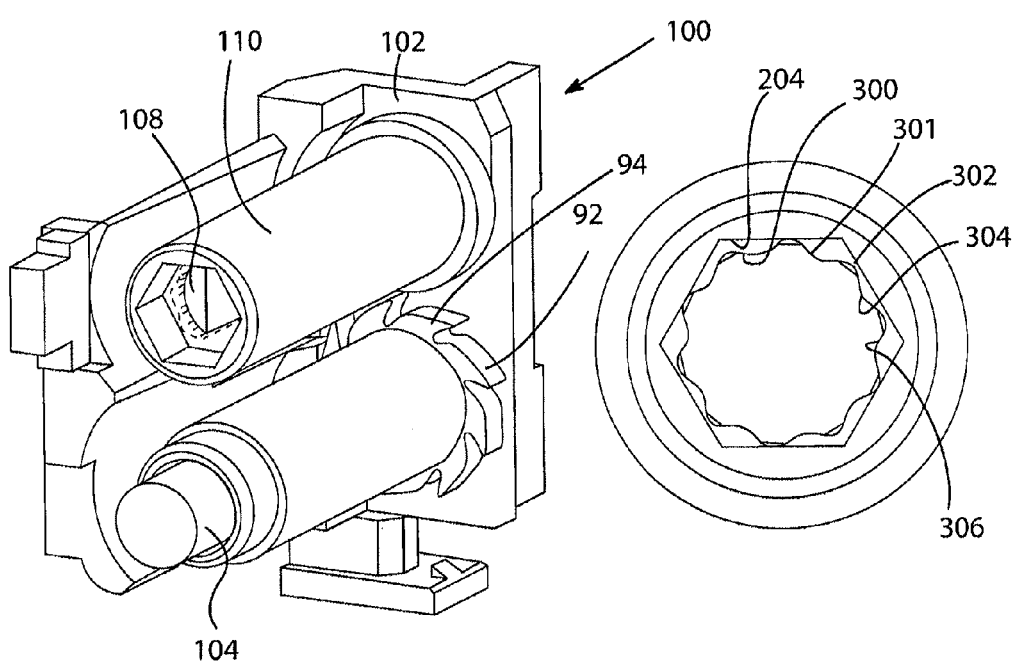
FIG. 16 shows an end view of the stock bobbin of FIG. 15.
FIG. 20 is an isometric view of the chassis assembled and including the stock bobbin of FIGS. 15 to 17 but excluding the tape for reasons of clarity.

It will be seen from FIG. 16 that the cross-sectional shape 301 is not symmetrical within the hexagonal socket 204. This has enabled the hexagonal socket 204 to be maintained at a useful size while still allowing the desired size and geometry of the cross section 301 to fit without interfering with the hexagonal shape of the hexagonal socket 204 and also permits moulding to work during manufacture.

Figure 17:
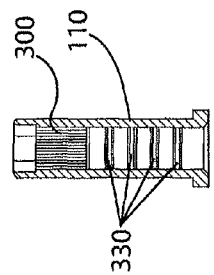
FIG. 17 is a section through a longitudinal axis of the stock bobbin of FIGS. 15 and 16.

As shown in FIG. 17, the stock bobbin 110 has a series of four circumferential ribs 330 inside it and a spaced therealong. These hold the stock bobbin 110 on the correct side of the mould tool during moulding.

Figure 21:
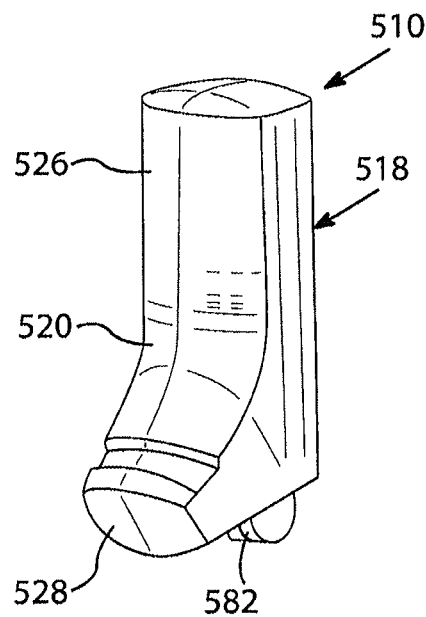
FIG. 21 is a view of a preferred embodiment of a dry powder inhaler in accordance with the present invention.
Figure 22:
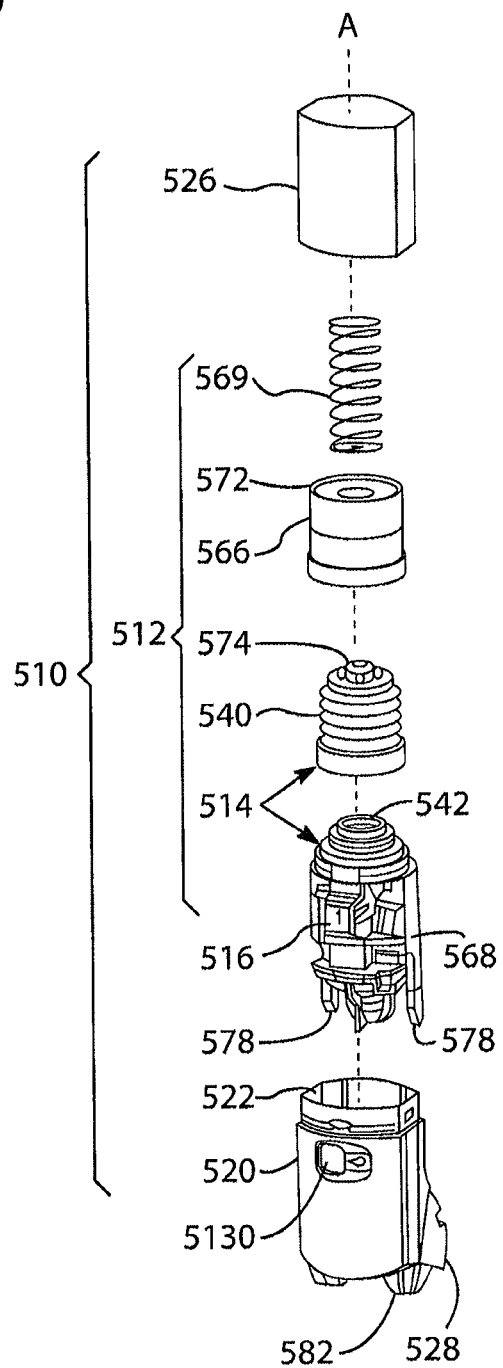
FIG. 22 is an exploded view of the inhaler of FIG. 21.
Figure 25:
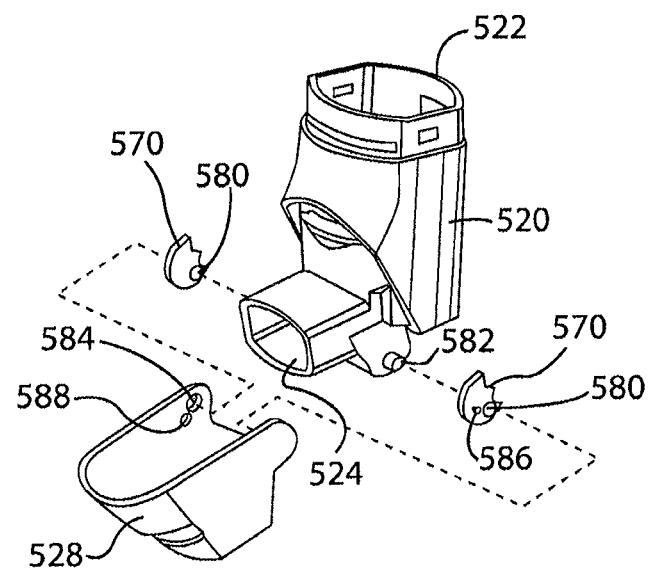
FIG. 25 is an exploded view of parts of the inhaler of FIG. 21.
Figure 26:
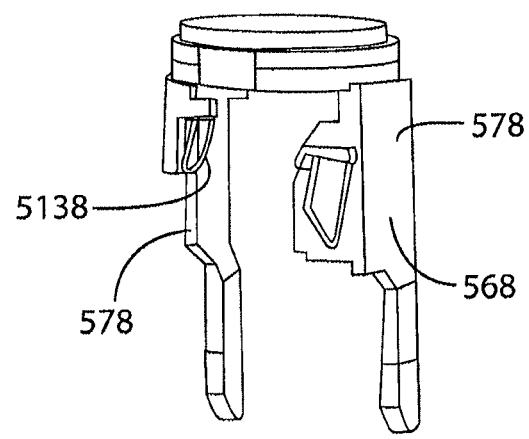
FIG. 26 is a view of a yoke of the inhaler of FIG. 21.

FIGS. 21 and 22 show a preferred embodiment in accordance with the invention of an inhaler 510 for dispensing a dry-powdered medicament in metered doses for patient inhalation. The inhaler 510 is as disclosed in FIGS. 1 to 16 or EP-A-1330280, the contents of which are hereby fully incorporated herein by reference, but with the stock bobbin 110 and second shaft 108 of the dose counter 516 modified so as to be as in FIGS. 15 to 20 hereof. Thus, the dry powder inhaler 510 generally includes a housing 518, and an assembly 512 received in the housing (see FIG. 21). The housing 518 includes a case 520 having an open end 522 and a mouthpiece 524 (FIG. 25) for patient inhalation, a cap 526 secured to and closing the open end 522 of the case 520, and a cover 528 pivotally mounted to the case 520 for covering the mouthpiece 524. As shown in FIG. 22, the inhaler 510 also includes an actuation spring 569, first yoke 566 with opening 572, bellows 540 with crown 574, a reservoir 514, second yoke 568 with hopper 542 and dose counter 516 mounted thereto, and case 520 has transparent window 5130 thereon for viewing dose counter tape indicia 5128. The dose metering system also includes two cams 570 mounted on the mouthpiece cover 528 and movable with the cover 528 between open and closed positions. The cams 570 each include an opening 580 for allowing outwardly extending hinges 582 of the case 520 to pass therethrough and be received in first recesses 584 of the cover 528. The cams 570 also include bosses 586 extending outwardly and received in second recesses 588 of the cover 528, such that the cover 528 pivots about the hinges 582 and the cams 570 move with the cover 528 about the hinges 582. As described in EP-A-1330280, cams 570 act upon cam followers 578 to move second yoke 568 up and down and thereby operate dose counter by engagement of pawl 5138 on the second yoke 568 with teeth 5136. Remaining components of the inhaler are provided as, and operate as described, in EP-A-1330280.

Figure 23:
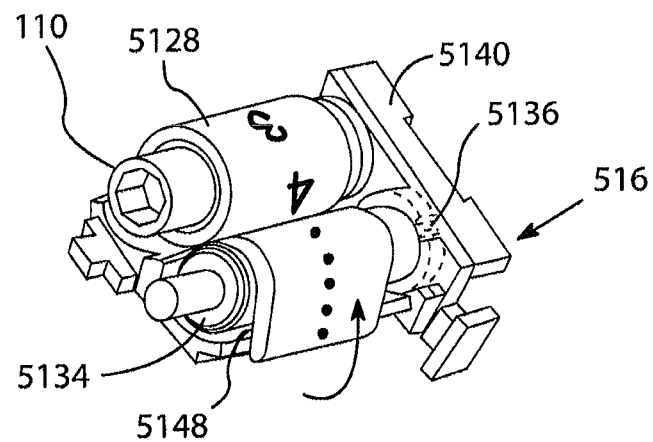
FIG. 23 is a view of a dose counter of the inhaler of FIG. 21.
Figure 24:
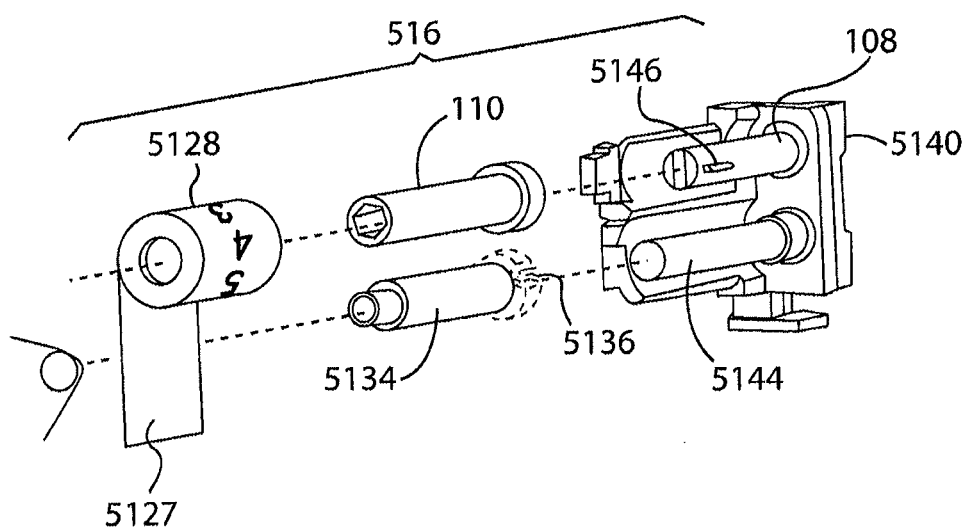
FIG. 24 is an exploded view of the dose counter shown in FIG. 23.

The dose counting system 516 therefore includes a ribbon or tape 5128 (FIGS. 23 & 24), having successive numbers or other suitable indicia printed thereon, in alignment with a transparent window 5130 provided in the housing 18 (see FIG. 22). The dose counting system 516 includes the rotatable stock bobbin 110 (as described above), an indexing spool 5134 rotatable in a single direction, and the ribbon 5128 rolled and received on the bobbin 110 and having a first end 5127 secured to the spool 5134, wherein the ribbon 5128 unrolls from the bobbin 110 so that the indicia are successively displayed as the spool 5134 is rotated or advanced. In FIGS. 23 and 24 the wavelike engagement surface 300 of the bobbin 110 is not shown for the purposes of clarity.

The spool 134 is arranged to rotate upon movement of the yokes 566, 568 to effect delivery of a dose of medicament from reservoir 514, such that the number on the ribbon 5128 is advanced to indicate that another dose has been dispensed by the inhaler 510. The ribbon 5128 can be arranged such that the numbers, or other suitable indicia, increase or decrease upon rotation of the spool 5134. For example, the ribbon 5128 can be arranged such that the numbers, or other suitable indicia, decrease upon rotation of the spool 5134 to indicate the number of doses remaining in the inhaler 510. Alternatively, the ribbon 5128 can be arranged such that the numbers, or other suitable indicia, increase upon rotation of the spool 5134 to indicate the number of doses dispensed by the inhaler 10.

The indexing spool 5134 includes radially extending teeth 5136, which are engaged by pawl 5138 extending from a cam follower 578 of the second yoke 568 upon movement of the yoke to rotate, or advance, the indexing spool 5134. More particularly, the pawl 5138 is shaped and arranged such that it engages the teeth 5136 and advances the indexing spool 5134 only upon the mouthpiece cover 528 being closed and the yokes 566, 568 moved back towards the cap 526 of the housing 518.

The dose counting system 516 also includes a chassis 5140 that secures the dose counting system to the hopper 542 and includes shafts 108, 5144 for receiving the bobbin 110 and the indexing spool 5134. As described above with reference to FIGS. 1 to 20, the bobbin shaft 108 is forked and includes radially nubs 5146 for creating a resilient resistance to rotation of the bobbin 110 on the shaft 108 by engaging with the wavelike engagement surface 300 inside the bobbin 110. A clutch spring 5148 is received on the end of the indexing spool 5134 and locked to the chassis 5140 to allow rotation of the spool 5134 in only a single direction.

Various modifications may be made to the embodiment shown without departing from the scope of the invention as defined by the accompanying claims as interpreted under patent law.

What is claimed:

1. A method of assembling an inhaler comprising a dose counter viewing window, the method comprising assembling a dose counter by:
   attaching one end of a tape to a tape stock bobbin, the tape having dosing indicia, tape positioning indicia, a tape size marker indicating a number of dosing indicia on the tape, and priming indicia, the priming indicia being located between the dosing indicia and a distal end of the tape;
   stowing the tape on the tape stock bobbin while monitoring for the tape positioning indicia and the tape size marker with a sensor;
   securing a tape reel shaft to the distal end of the tape;
   mounting the tape stock bobbin and the tape reel shaft onto separate shafts of the dose counter of the inhaler; and
   winding the tape reel shaft until the priming indicia on the tape is in a position to be located in the window when the inhaler is fully assembled,
   wherein the dose counter so assembled is subsequently inserted into the inhaler.

2. The method of claim 1, wherein the sensor is a camera or laser scanner.

3. The method of claim 1 further comprising transmitting data relating to the tape positioning indicia, by the sensor, to a computer controller.

4. The method of claim 3 further comprising winding the tape, by a motor, onto the tape stock bobbin.

5. The method of claim 4 further comprising the stopping the motor, by the computer controller, when the tape is nearly fully wound onto the bobbin.

6. The method of claim 1 further comprising logging details of the tape in a stocking system data store, the details including a number of tape positioning indicia on the tape.

7. The method of claim 1, wherein the tape positioning indicia are a series of lines that extend across the tape.

8. The method of claim 1, wherein the tape size marker is located between the tape positioning indicia and the distal end of the tape.

9. A method of assembling an inhaler comprising a dose counter and a dose counter viewing window, the method comprising:
   assembling a dose counter by:
   (i) attaching one end of a tape to the stock bobbin, the tape having dosing indicia, a tape size marker indicating a number of dosing indicia on the tape, and tape positioning indicia, the tape positioning indicia being located between the dosing indicia and a distal end of the tape;
   (ii) stowing the tape on the stock bobbin while monitoring for the tape positioning indicia and the tape size marker with a sensor,
   (iii) securing a tape reel shaft to the distal end of the tape,
   (iv) mounting the tape stock bobbin and the tape reel shaft onto separate shafts of the dose counter of the inhaler, and
   (v) winding the tape reel shaft until the tape is in a position wherein a portion of the tape between the distal end of the tape and the dosing indicia will be located in the window when the inhaler is fully assembled; and
   wherein the dose counter so assembled is subsequently inserted into the inhaler.

10. The method of claim 9, wherein the tape size marker is located between the tape positioning indicia and the distal end of the tape.

* * * * *